United States Patent [19]

Zanetti et al.

[11] Patent Number: 5,306,812
[45] Date of Patent: Apr. 26, 1994

[54] IMMUNOGLOBULIN-BINDING POLYPEPTIDES

[75] Inventors: Maurizio Zanetti, La Jolla, Calif.;
Petar Lenert, NoviSad, Yugoslavia;
Edward Golub, La Jolla, Calif.;
Daniel Kroon, Bridgewater, N.J.

[73] Assignee: The Regents of the University of California, Oakland, Calif.

[21] Appl. No.: 541,269

[22] Filed: Jun. 20, 1990

Related U.S. Application Data

[63] Continuation-in-part of Ser. No. 404,968, Sep. 8, 1989, Pat. No. 5,231,167.

[51] Int. Cl.$^5$ .................... C07K 15/28; C07K 3/18; C07K 3/00; A61K 37/02
[52] U.S. Cl. .................... 530/413; 530/300; 530/350; 530/387.1
[58] Field of Search ............... 530/413, 387, 350, 300, 530/387.1

[56] References Cited

PUBLICATIONS

Maddon et al Cell vol. 42, 93–104, 1985.
Byrn et al. Nature vol. 344 667–670.
Nilsson et al Embo Journal 4, 1075–1080 1985.
Capon et al. Nature vol. 337, 9th Feb. 1989 pp. 525–530.
Guss, et al., The EMBO Journal, 5, 1567–1575 (1986).
Uhlen, et al., Journal of Biol. Chem. 259, 1695–1702 (1984).
Lamarre, et al., Science, vol. 245, 743–746 (1989).

*Primary Examiner*—David L. Lacey
*Assistant Examiner*—Lila Feisee
*Attorney, Agent, or Firm*—Walter H. Dreger

[57] ABSTRACT

A method of separating $V_H$ containing immunoglobulins by admixing an immunoglobulin binding peptide is described. The polypeptide of the invention is capable of binding to heavy chain variable regions of antibodies in an antigen independent manner and can separate antigen/antibody complexes.

4 Claims, 19 Drawing Sheets

```
CAAGCCCAGAGCCCTGCCATTTCTGTGGGCTCAGTCCCTACTGCTCAGCCCCTTCCTCCTCGGCAAGGCCACA                                                                    108
                                                          met asn arg gly val pro phe arg his leu leu
                                                          ATG AAC CGG GGA GTC CCT TTT AGG CAC TTG CTT
                       -10              -1  +1                        -20
leu val leu gln leu ala leu pro ala ala thr gln gly lys lys val val leu gly lys val gly asp thr val glu leu thr lys cys    198
CTG GTG CTG CAA CTG GCG CTC CCA GCA GCC ACT CAG GGA AAG AAA GTG GTG CTG GGC AAA GTA GTG GAT ACA GTG GAA CTG ACC AAG TGT
          +20                                      +30                                +40                                *
thr ala ser gln lys ser lys lys ile gln phe his trp lys asn ser asn gln ile leu gly asn gly ser phe leu thr lys            288
ACA GCT TCC CAG AAG AGC AAG AAG ATA CAA TTC CAC TGG AAA AAC TCC AAC CAG ATA AAG ATT CTG GGA AAT GGG TCC TTC TTA ACT AAA
             +50                                   +60                                +70
gly pro ser lys leu asn asp arg ala asp ser arg arg ser leu trp asp gln gly asn phe pro leu ile ile lys asn leu lys ile    378
GGT CCA TCC AAG CTG AAT GAT CGC GCT GAC AGC CTT GAC CAA AGA AGA AGC CTG TGG GAC CAA GGA AAC TTC CCC CTG ATC ATC AAG AAT CTT AAG ATA
             +80                    *                                +90                                +100
glu asp ser asp thr tyr ile cys glu val glu asp gln lys glu glu val gln leu leu val phe gly leu thr ala asn ser asp thr    468
GAA GAC TCA GAT ACT TAC ATC TGT GAA GTG GAG GAC CAG AAG GAG GAG GTG CAA TTG CTA GTG TTC GGA TTG ACT GCC AAC TCT GAC ACC
          +110                                     +120                                    *  +131
his leu gln gly gln ser leu thr leu thr leu glu ser pro pro gly ser ser pro ser val gln cys arg ser pro arg gly lys        558
CAC CTG CTT CAG GGG CAG AGC CTG ACC CTG ACC CTG GAG AGC CCC CCT GGT AGC AGT CCC TCA GTG CAA TGT AGG AGT CCA AGG GGT AAA
          +140                                     +150                                +160
asn ile gln gly gly lys thr leu ser val ser gln leu glu leu gln asp ser gly thr trp thr cys thr val leu gln asn gln lys    648
AAC ATA CAG GGG GGA AAG ACC CTC TCC GTG TCT CAG CTG GAG CTC CAG GAT AGT GGC ACC TGG ACA TGC ACT GTC TTG CAG AAC CAG AAG
          +170                                     +180                                +190
lys val glu phe lys ile asp ile val val leu ala phe gln lys ala ser ser ile val tyr lys lys glu gly glu gln val glu phe    738
AAG GTG GAG TTC AAA ATA GAC ATC GTG GTG CTA GCT TTC CAG AAG GCC TCC AGC ATA GTC TAT AAG AAA GAG GGG GAA CAG GTG GAG TTC
          +200                                     +210                                +220
ser phe pro leu ala phe thr val glu lys leu thr gly ser gly glu leu trp trp gln ala glu arg ala ser ser ser lys ser trp    828
TCC TTC CCA CTC GCC TTT ACA GTT GAA AAG CTG ACG GGC AGT GGC GAG CTG TGG TGG CAG GCG GAG AGG GCT TCC TCC AAG TCT TGG
          +230                                     +240                                +250
ile thr phe asp leu lys asn lys glu val ser val lys arg val thr gln asp pro lys leu gln met gly lys lys leu pro leu his    918
ATC ACC TTT GAC CTG AAG AAC AAG GAA GTG TCT GTA AAA CGG GTT ACC CAG GAC CCT AAG CTC CAG ATG GGC AAG AAG CTC CCG CTC CAC
```

FIG.IA-I

```
+260                        +270 CHO                      +280
leu thr leu pro gln ala gly ser gly asn leu thr leu ala leu glu ala lys thr gly lys leu his gln glu
CTC ACC CTG CCC CAG GCC TCT GGC TGG AAC CTC ACC CTG GCC CTT GAA GCG AAA GGA AAG TTG CAT CAG GAA    1008
                       +290              CHO    *              +310
val asn leu val val met arg ala thr gln leu gln lys asn leu thr cys glu val trp gly pro thr ser pro lys leu met leu ser
GTG AAC CTG GTG GTG ATG AGA GCC ACT CAG CTC CAG AAA AAT CTC ACC TGT GAG GTG TGG GGA CCC ACC TCC CCT AAG CTG ATG CTG AGC    1098
                 +320                      +330                    *            +340
leu lys leu glu asn lys val glu ala lys val ser lys arg glu glu ala lys arg pro val leu asn pro glu ala gly met trp gln cys leu
TTG AAA CTG GAG AAC AAG GTG GAG GCA AAG GTC TCG AAG CGG GAG GAG GCG AAG CGG CCT GTG CTG AAC CCG GAG GCG GGG ATG TGG CAG TGT CTG    1188
              +350                        +360                      +370
leu ser asp ser gly gln val leu leu glu ser asn ile leu lys val leu pro thr trp ser thr pro val gln pro met ala leu ile val
CTG AGT GAC TCG GGA CAG GTC CTG CTG GAA TCC AAC ATC CTG AAG GTT CTG CCC ACA TGG TCC ACC CCG GTG CAG CCA ATG GCC CTG ATT GTG    1278
                +380                    +390                    +400
leu gly gly val ala gly leu leu leu leu phe ile gly leu gly ile phe phe cys val arg cys arg arg arg his arg gln ala glu arg
CTG GGG GGC GTC GCC GGC CTC CTG CTG CTT TTC ATT GGG CTA GGC ATC TTC TTC TGT GTC AGG TGC AGG CGG CAC CGA AGG CGC CAA GCA GAG CGG    1368
                TM                                          CYT
      +410                    +420                        +430
met ser gln ile lys arg leu leu ser glu lys lys thr cys gln cys pro his arg phe gln lys thr cys ser pro ile ---
ATG TCT CAG ATC AAG AGA CTC CTC AGT GAG AAG AAG ACC TGC CAG TGC CCT CAC CGG TTT CAG AAG ACA TGT AGC CCC ATT TGA GGCACGA    1459
                                                          CYT GGCCAGGCAGATCCCACTTGAGCCTCGCCGGTTCCTGCCTGCGGACCAGATGAATGAGCAGATCCCACGCTCTGGCCTCTGTCGTCCTCCTACAATTTG    1578

CCATTGTTCTCTGGGTTAGGCCCGGCTTCACTGGTTGAGTGTTGCTCTCTAGTTCCAGAGGCTTAATCACACCCTCCTCCACGCCATTTCCTTTCCTTCAAGCCTAGCCCTTCT    1697

CTCATTATTCTCTGACCCTCTCCCCACTGCTGCTCATTGGATCC    1742
```

FIG. 1A-2

```
TaqI
TCGAAATAGGCGTGATTTTGCGGTTTTAAGCCTTTTACTTCCTGAATAAATCTTTCAGCAAAATATTATTT
                                                                         - - - - -     72

-35    -35            -10
ATAAGTTGTAAAACTTACCTTTAAATTTAATTATAAATATAGATTTAGTATTGCAATACATAATTCGTAT     144

-10                                                S
ATTATGATGACTTTACAAATACACAGGGGGTATTAATTTGAAAGAAAAACATTTATTCAATTCGTAAA
                        ══════════════        └→
                                                LeuLysLysAsnIleTyrSerIleArgLys     216
                                                -36

CTAGGTGTAGGTATTGCATCTGTAACTTTAGGTACATTACTTATATCTGGTGGCGTAACACCTGCTGCAAAT
LeuGlyValGlyIleAlaSerValThrLeuGlyThrLeuLeuIleSerGlyGlyValThrProAlaAlaAsn     288
-20
```

FIG. 2A-1

```
AAAGAACAACAAAATGCTTTCTATGAAATTTTACATTTACCTAACTTAACTGAAGAACAACGTAACGGCTTC        1080
LysGluGlnGlnAsnAlaPheTyrGluIleLeuHisLeuProAsnLeuThrGluGluGlnArgAsnGlyPhe
240                                                      260

ATCCAAAGCCTTAAAGACGATCCTTCGGTGAGCAAAGAAATTTTAGCAGAAGCTAAAAAGCTAAACGATGCT        1152
IleGlnSerLeuLysAspAspProSerValSerLysGluIleLeuAlaGluAlaLysLysLeuAsnAspAla
                               200

┌──→ X
CAAGCACCAAAAGAGGAAGACAATAACAAGCCTGGCAAAGAAGACAATAACAAGCCTGGCAAAGAAGACAAT        1224
GlnAlaProLysGluGluAspAsnAsnLysProGlyLysGluAspAsnAsnLysProGlyLysGluAspAsn
                                    300

AACAAGCCTGGCAAAGAAGACAACAACAAGCCTGGCAAAGAAGACAACAACAAGCCTGGTAAAGAAGACAAC        1296
AsnLysProGlyLysGluAspAsnAsnLysProGlyLysGluAspAsnAsnLysProGlyLysGluAspAsn
                        320

AACAAGCCTGGCAAAGAAGACGGCAACAAGCCTGGTAAAGAAGACAACAAAAAACCTGGTAAAGAAGATGGC        1360
AsnLysProGlyLysGluAspGlyAsnLysProGlyLysGluAspAsnLysLysProGlyLysGluAspGly
                       340

AACAAGCCTGGTAAAGAAGACAACAAAAAACCTGGTAAAGAAGACGGCAACAAGCCTGGCAAAGAAGATGGC        1440
AsnLysProGlyLysGluAspAsnLysLysProGlyLysGluAspGlyAsnLysProGlyLysGluAspGly
360                                                300

AACAAACCTGGTAAAGAAGATGGTAACGGAGTACATGTCGTTAAACCTGGTGATACAGTAAATGACATTGCA        1512
AsnLysProGlyLysGluAspGlyAsnGlyValHisValValLysProGlyAspThrValAsnAspIleAla
                                            400

PstI                    BclI
AAAGCAAACGGCACTACTGCTGACAAAATTGCTGCAGATAACAAATTAGCTGATAAAAACATGATCAAACCT        1584
LysAlaAsnGlyThrThrAlaAspLysIleAlaAlaAspAsnLysLeuAlaAspLysAsnMetIleLysPro
                            420

GGTCAAGAACTTGTTGTTGATAAGAAGCAACCACAAACCATGCAGATGCTAACAAAGCTCAAGCATTACCAG        1656
GlyGlnGluLeuValValAspLysLysGlnProGlnThrMetGlnMetLeuThrLysLeuLysHisTyrGln
                                440

AAACTGGCGAAGAAAATCCATTCATCGGTACAACTGTATTTGGTGGATTATCATTAGCCTTAGGTGCAGCGT        1728
LysLeuAlaLysLysIleHisSerSerValGlnLeuTyrLeuValAspTyrHisEND
460

EcoRV
TATTAGCTGGACGTCGTCGCGAACTATAAAAACAAACAATACACAACGATAGATATCATTTTATGCAAACCA        1800

ATTTTAACTTATATACGTTGATTAACACATTCTTATTTGAAATGATAAGAATCATCTAAATGCACGAGCAAC        1872
                                                       - - - - - - - -

ATCTTTTGTTGCTCAGTGCATTTTTTATTTTACTTACTTTTCTAAACA                                1920
- - - - - - - - - -
```

```
EcoRI         ┌──→A1
CAA TTC AAC│AAA TAT GGA GTA AGT GAC TAT TAC AAG AAT CTA ATC          45
Glu Phe Asn Lys Tyr Gly Val Ser Asp Tyr Tyr Lys Asn Leu Ile
                                            ┌──→B1
AAC AAT GCC AAA ACT GTT GAA GGC GTA AAA GAC CTT│CAA GCA CAA          90
Asn Asn Ala Lys Thr Val Glu Gly Val Lys Asp Leu Gln Ala Gln

GTT GTT GAA TCA GCG AAG AAA GCG CGT ATT TCA GAA GCA ACA GAT         135
Val Val Glu Ser Ala Lys Lys Ala Arg Ile Ser Glu Ala Thr Asp

GGC TTA TCT GAT TTC TTG AAA TCA CAA ACA CCT GCT GAA GAT ACT         180
Gly Leu Ser Asp Phe Leu Lys Ser Gln Thr Pro Ala Glu Asp Thr

GTT AAA TCA ATT GAA TTA GCT GAA GCT AAA GTC TTA GCT AAC AGA         225
Val Lys Ser Ile Glu Leu Ala Glu Ala Lys Val Leu Ala Asn Arg
              ┌──→A2
GAA CTT GAC│AAA TAT GGA GTA AGT GAC TAT CAC AAG AAC CTA ATC         270
Glu Leu Asp Lys Tyr Gly Val Ser Asp Tyr His Lys Asn Leu Ile
                                            ┌──→B2
AAC AAT GCC AAA ACT GTT GAA GGT GTA AAA GAC CTT│CAA GCA CAA         315
Asn Asn Ala Lys Thr Val Glu Gly Val Lys Asp Leu Gln Ala Gln

GTT GTT GAA TCA GCG AAG AAA GCG CGT ATT TCA GAA GCA ACA GAT         360
Val Val Glu Ser Ala Lys Lys Ala Arg Ile Ser Glu Ala Thr Asp

GGC TTA TCT GAT TTC TTG AAA TCA CAA ACA CCT GCT GAA GAT ACT         405
Gly Leu Ser Asp Phe Leu Lys Ser Gln Thr Pro Ala Glu Asp Thr

GTT AAA TCA ATT GAA TTA GCT GAA GCT AAA GTC TTA GCT AAC AGA         450
Val Lys Ser Ile Glu Leu Ala Glu Ala Lys Val Leu Ala Asn Arg
              ┌──→A3
GAA CTT GAC│AAA TAT GGA GTA AGT GAC TAT TAC AAG AAC CTA ATC         495
Glu Leu Asp Lys Tyr Gly Val Ser Asp Tyr Tyr Lys Asn Leu Ile
                                        ┌──→S
AAC AAT GCC AAA ACT GTT GAA GGT GTA AAA GCA CTG│ATA GAT GAA         540
Asn Asn Ala Lys Thr Val Glu Gly Val Lys Ala Leu Ile Asp Glu
                                    ┌──→C1
ATT TTA GCT GCA TTA CCT AAG ACT GAC│ACT TAC AAA TTA ATC CTT         585
Ile Leu Ala Ala Leu Pro Lys Thr Asp Thr Tyr Lys Leu Ile Leu

AAT GGT AAA ACA│TTG│AAA GGC GAA ACA ACT ACT GAA GCT GTT GAT         630
Asn Gly Lys Thr│Leu│Lys Gly Glu Thr Thr Thr Glu Ala Val Asp
              PstI

GCT GCT ACT GCA GAA AAA GTC TTC AAA CAA TAC GCT AAC GAC AAC         675
Ala Ala Thr Ala Glu Lys Val Phe Lys Gln Tyr Ala Asn Asp Asn

GGT GTT GAC GGT GAA TGG ACT TAC GAC GAT GCG ACT AAG ACC TTT         720
Gly Val Asp Gly Glu Trp Thr Tyr Asp Asp Ala Thr Lys Thr Phe
              ┌──→D1              ClaI
ACA GTT ACT GAA│AAA CCA GAA GTG ATC GAT GCG TCT GAA TTA ACA         765
Thr Val Thr Glu Lys Pro Glu Val Ile Asp Ala Ser Glu Leu Thr
              ┌──→C2
CCA GCC GTG ACA│ACT TAC AAA CTT GTT ATT AAT GGT AAA ACA│TTG│        810
Pro Ala Val Thr Thr Tyr Lys Leu Val Ile Asn Gly Lys Thr│Leu│
```

FIG. 3A-1

```
                                                    PstI
AAA GGC GAA ACA ACT ACT GAA GCT GTT GAT GCT GCT ACT GCA GAA      855
Lys Gly Glu Thr Thr Thr Glu Ala Val Asp Ala Ala Thr Ala Glu

AAA GTC TTC AAA CAA TAC GCT AAC GAC AAC GGT GTT GAC GGT GAA      900
Lys Val Phe Lys Gln Tyr Ala Asn Asp Asn Gly Val Asp Gly Glu
                                                         ┌──→D2
TGG ACT TAC GAC GAT GCG ACT AAG ACC TTT ACA GTT ACT GAA│AAA      945
Trp Thr Tyr Asp Asp Ala Thr Lys Thr Phe Thr Val Thr Glu Lys
              ClaI                                   ┌──→C3
CCA GAA GTG ATC GAT GCG TCT GAA TTA ACA CCA GCC GTG ACA│ACT      990
Pro Glu Val Ile Asp Ala Ser Glu Leu Thr Pro Ala Val Thr Thr

TAC AAA CTT GTT ATT AAT GGT AAA ACA TTG AAA GGC GAA ACA ACT     1035
Tyr Lys Leu Val Ile Asn Gly Lys Thr Leu Lys Gly Glu Thr Thr
                              PstI
ACT AAA GCA GTA GAC GCA GAA ACT GCA GAA AAA GCC TTC AAA CAA     1080
Thr Lys Ala Val Asp Ala Glu Thr Ala Glu Lys Ala Phe Lys Gln

TAC GCT AAC GAC AAC GGT GTT GAT GGT GTT TGG ACT TAT GAT GAT     1125
Tyr Ala Asn Asp Asn Gly Val Asp Gly Val Trp Thr Tyr Asp Asp
                                   ┌──→W
GCG ACT AAG ACC TTT ACG GTA ACT GAA│ATG GTT ACA GAG GTT CCT     1170
Ala Thr Lys Thr Phe Thr Val Thr Glu Met Val Thr Glu Val Pro

GGT GAT GCA CCA ACT GAA CCA GAA AAA CCA GAA GCA AGT ATC CCT     1215
Gly Asp Ala Pro Thr Glu Pro Glu Lys Pro Glu Ala Ser Ile Pro
         HoaI
CTT GTT CCG TTA ACT CCT GCA ACT CCA ATT GCT AAA GAT GAC GCT     1260
Leu Val Pro Leu Thr Pro Ala Thr Pro Ile Ala Lys Asp Asp Ala

AAG AAA GAC GAT ACT AAG AAA GAA GAT GCT AAA AAA CCA GAA GCT     1305
Lys Lys Asp Asp Thr Lys Lys Glu Asp Ala Lys Lys Pro Glu Ala

AAG AAA GAA GAC GCT AAG AAA GCT GAA ACT CTT CCT ACA ACT GGT     1350
Lys Lys Glu Asp Ala Lys Lys Ala Glu Thr Leu Pro Thr Thr Gly
                        ┌──→M           PvuII
GAA GGA AGC AAC│CCA TTC TTC ACA GCA GCT GCG CTT GCA GTA ATG     1395
Glu Gly Ser Asn Pro Phe Phe Thr Ala Ala Ala Leu Ala Val Met

GCT GGT GCG GGT GCT TTG GCG GTC GCT TCA AAA CGT AAA GAA GAC     1440
Ala Gly Ala Gly Ala Leu Ala Val Ala Ser Lys Arg Lys Glu Asp
                  HindIII
TAA TTGTCATTATTTTTGACAAAAAGCTT                                  1469
***
```

Positions 1–16:

|     | 1 | 2 | 3 | 4 | 5 | 6 | 7 | 8 | 9 | 10 | 11 | 12 | 13 | 14 | 15 | 16 |
|-----|---|---|---|---|---|---|---|---|---|----|----|----|----|----|----|----|
| C1 codon | ACT | TAC | AAA | TTA | ATC | CTT | AAT | GGT | AAA | ACA | TTG | AAA | GGC | GAA | ACA | ACT |
| C1 aa | Thr | Tyr | Lys | Leu | Ile | Leu | Asn | Gly | Lys | Thr | Leu | Lys | Gly | Glu | Thr | Thr |
| C2  | –   | –   | –   | *   | *   | –   | –   | –   | –   | –   | –   | –   | –   | –   | –   | –   |
|     |     |     |     | Val | Ile |     |     |     |     |     |     |     |     |     |     |     |
| C3  | –   | –   | –   | *   | *   | –   | –   | –   | –   | –   | –   | –   | –   | –   | –   | –   |
|     |     |     |     | Val | Ile |     |     |     |     |     |     |     |     |     |     |     |

Positions 17–32:

|     | 17 | 18 | 19 | 20 | 21 | 22 | 23 | 24 | 25 | 26 | 27 | 28 | 29 | 30 | 31 | 32 |
|-----|---|---|---|---|---|---|---|---|---|---|---|---|---|---|---|---|
| C1 codon | ACT | GAA | GCT | GTT | GAT | GCT | GCT | ACT | GCA | GAA | AAA | GTC | TTC | AAA | CAA | TAC |
| C1 aa | Thr | Glu | Ala | Val | Asp | Ala | Ala | Thr | Ala | Glu | Lys | Val | Phe | Lys | Gln | Tyr |
| C2  | –   | *   | –   | *   | *   | –   | –   | –   | –   | –   | –   | –   | –   | –   | –   | –   |
|     |     | Lys |     | *   | Glu |     |     |     |     |     |     |     |     |     |     |     |
| C3  | –   | –   | –   | –   | –   | –   | –   | –   | –   | –   | –   | –   | –   | –   | –   | –   |
|     |     |     |     |     |     |     |     |     |     | Ala |     |     |     |     |     |     |

Positions 33–48:

|     | 33 | 34 | 35 | 36 | 37 | 38 | 39 | 40 | 41 | 42 | 43 | 44 | 45 | 46 | 47 | 48 |
|-----|---|---|---|---|---|---|---|---|---|---|---|---|---|---|---|---|
| C1 codon | GCT | AAC | GAC | AAC | GGT | GTT | GAC | GGT | GAA | TGG | ACT | TAC | GAC | GAT | GCG | ACT |
| C1 aa | Ala | Asn | Asp | Asn | Gly | Val | Asp | Gly | Glu | Trp | Thr | Tyr | Asp | Asp | Ala | Thr |
| C2  | –   | –   | –   | –   | –   | –   | –   | –   | –   | –   | –   | –   | –   | *   | –   | –   |
| C3  | –   | –   | –   | –   | –   | –   | –   | –   | –   | –   | *   | –   | –   | *   | –   | –   |
|     |     |     |     |     |     |     |     |     |     |     | Val |     |     |     |     |     |

Positions 49–55:

|     | 49 | 50 | 51 | 52 | 53 | 54 | 55 |
|-----|----|----|----|----|----|----|----|
| C1 codon | AAG | ACC | TTT | ACA | GTT | ACT | GAA |
| C1 aa | Lys | Thr | Phe | Thr | Val | Thr | Glu |
| C2  | –   | –   | *   | –   | *   | –   | –   |
| C3  | –   | –   | –   | –   | –   | –   | –   |

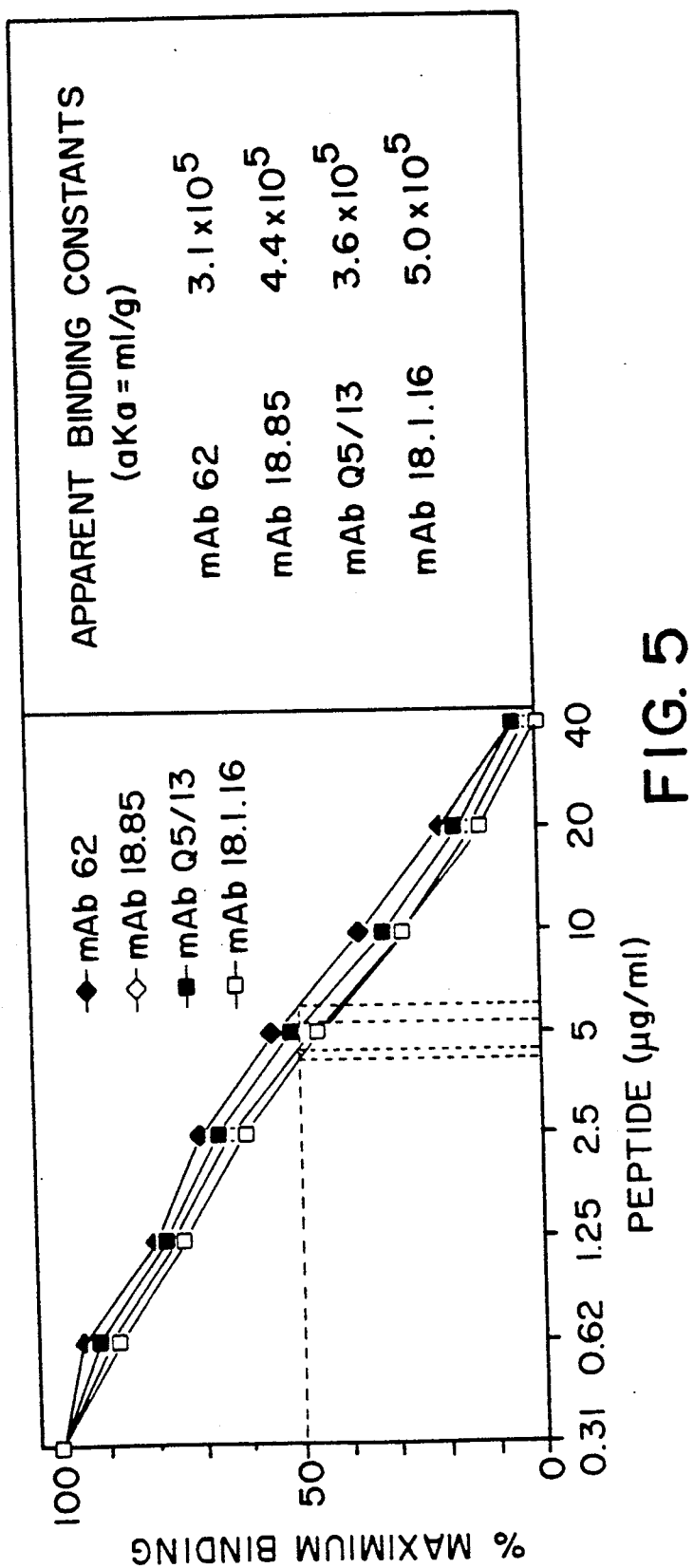

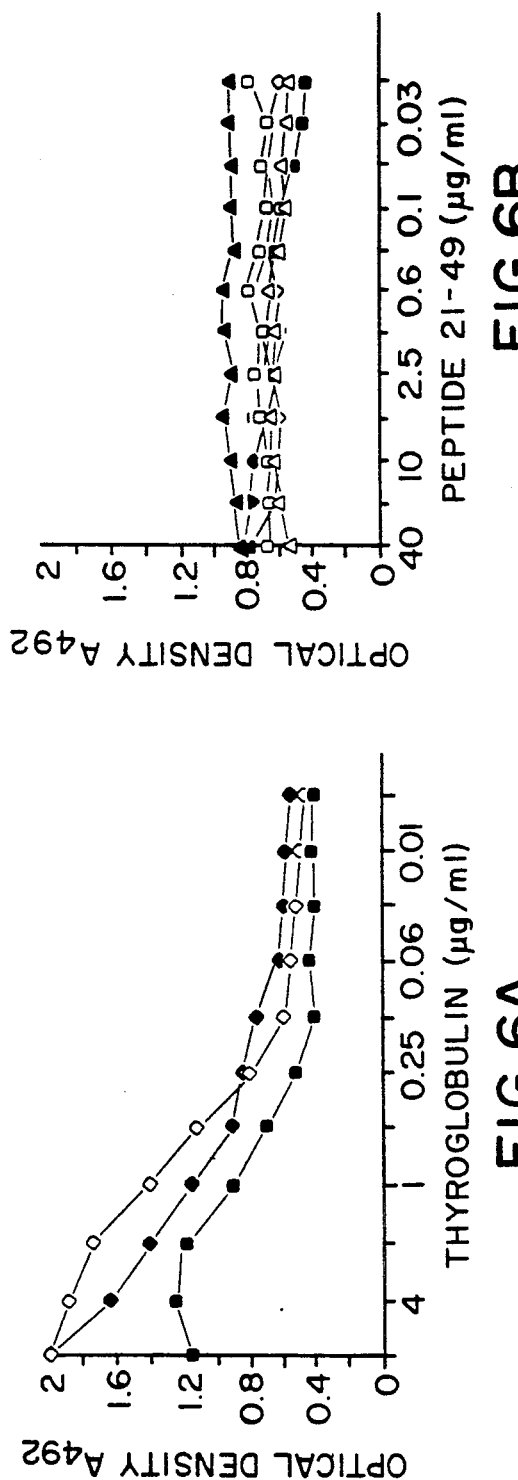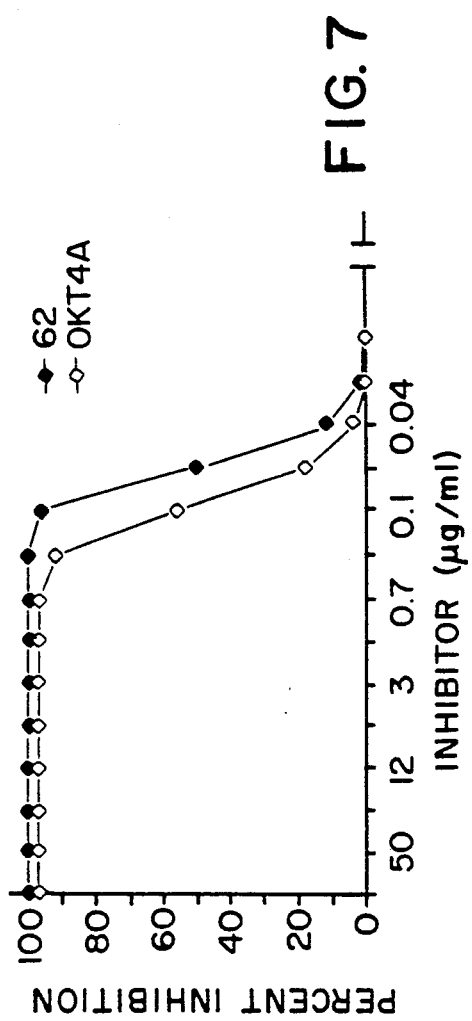

FIG.10

```
G   S   Q   K   K   S   I   Q   F   H   W   K   N   S   N   Q
Gly Ser Gln Lys Lys Ser Ile Gln Phe His Try Lys Asn Ser Asn Gln
GA  TCC CAA AAA AAA AGT ATC CAA TTC CAT TGG AAA AGT AAC CAA
    GTT TTT TTT TCA TAG GTT AAG GTA ACC TTT TCA TTG CAA GTT

I   K   K   G   N   Q   G   S   F   L   T   K   G   P
Ile Lys Lys Gly Asn Gln Gly Ser Phe Leu Thr Lys Gly Pro
ATC AAA AAA GGT AAC CAA GGT AGT TTC TTA ACT AAA GGT CCT
TAG TTT TTT CCA TTG GTT CCA TCA AAG AAT TGC TTT CCA GGA

S   G   S
Ser Gly Ser
AGT G
TCA CCT AC
```

```
Gly Phe Ile Asp Ala Ser Glu Leu Thr Pro Ala Val Thr Thr Tyr Lys Leu Val Ile Asn
AA  TTC ATC GAT GCG TCT GAA TTA ACA CCA GCC GTG ACA ACT TAC AAA CTT GTT ATT AAT
  G TAG CTA CGC AGA CTT AAT TGT GGT CGG CAC TGT TGA ATG TTT GAA CAA TAA TTA

Gly Lys Thr Leu Lys Gly Glu Thr Thr Thr Glu Ala Val Thr Ala Ala Thr Ala Glu Lys
GGT AAA ACA TTG AAA GGC GAA ACA ACT GAT GAA GCT GTT GAT GCT GCT ACT GCA GAA AAA
CCA TTT TGT AAC TTT CCG CTT TGT TGA CTA CTT CGA CAA CTA CGA CGA TGA CGT CTT TTT

Val Phe Lys Gln Tyr Ala Asn Asp Asn Gly Val Asp Gly Glu Trp Thr Tyr Asp Asp Ala
GTC TTC AAA CAA TAC GCT AAC GAC AAC GGT GTT GAC GGT GAA TGG ACT TAC GAC GAT GCG
CAG AAG TTT GTT ATG CGA TTG CTG TTG CCA CAA CTG CCA CTT ACC TGA ATG CTG CTA CGC

Thr Lys Thr Phe Thr Val Thr Glu Lys Pro Glu Val Ile Asp Gly Ser Glu Phe
ACT AAG ACC TTT ACA GTT ACT GAA AAA CCA GAA GTG ATC GAT GGA TCC G
TGA TTC TGG AAA TGT CAA TGA CTT TTT GGT CTT CAC TAG CCT AGG CTT AA
```

FIG.12

```
Gly Ser Ile Asp Ala Ser Glu Leu Thr Pro Ala Val Thr Tyr Lys Leu Val Ile Asn
GA  TCC ATC GAT GCG TCT GAA TTA ACA CCA GCC GTG ACA TAC AAA CTT GTT ATT AAT
 G  TAG CTA CGC AGA CTT AAT TGT GGT CGG CAC TGT ATG TTT GAA CAA TAA TTA

Gly Lys Leu Lys Gly Glu Thr Thr Glu Ala Val Asp Ala Ala Thr Ala Glu Lys
GGT AAA TTG AAA GGC GAA ACA ACT GAA GCT GTT GAT GCT ACT GCA GAA AAA
CCA TTT AAC TTT CCG CTT TGT TGA CTT CGA CAA CTA CGA TGA CGT CTT TTT

Val Phe Lys Gln Tyr Ala Asn Asp Gly Val Asp Gly Glu Trp Thr Tyr Asp Ala
GTC TTC AAA CAA TAC GCT AAC GAC GGT GTT GAC GGT GAA TGG ACT TAC GAT GCG
CAG AAG TTT GTT ATG CGA TTG CTG CCA CAA CTG CCA CTT ACC TGA ATG CTA CGC

Thr Lys Phe Thr Val Thr Glu Lys Pro Glu Val Ile Asp Gly Ser Arg Ser
ACT AAG TTT ACA GTT ACT GAA AAA CCA GAA GTG ATC GAT GGA TCC C
TGA TTC AAA TGT CAA TGA CTT TTT GGT CTT CAC TAG CTA CCT AGG AG
```

FIG. 13

IMMUNOGLOBULIN-BINDING POLYPEPTIDES

CROSS REFERENCE TO RELATED APPLICATION

This is a continuation-in-part application of copending application Ser. No. 07/404,968, now allowed U.S. Pat. No. 5,231,167, having the same title and filed Sep. 8, 1989, the disclosure of which is hereby incorporated by reference.

TECHNICAL FIELD

The present invention relates to a new class of immunoglobulin-binding polypeptides, more particularly, the present invention relates to synthetic polypeptides and chimeric proteins capable of binding an immunoglobulin (Ig) molecule independent of the Ig molecule's antigen specificity.

BACKGROUND

The CD4 receptor is a non-polymorphic glycoprotein having a molecular weight of about 60,000 daltons that is present primarily on the surface of T lymphocytes with helper/inducer function. Structurally, it consists of three segments: extracellular, transmembrane and cytoplasmic. The former comprises four immunoglobulin (Ig) variable (V) region-like domains of which the first, second and forth are linked by disulfide bonds. Because of sequence and structure homology with the V domain of Ig light (L) chain, it has been proposed that the gene coding for the CD4 molecule is a member of the Ig supergene family.

While it is clear that CD4 is a receptor that binds biologically important molecules, its physiological role is not fully understood.

Although it was long suspected that CD4 may function as a receptor molecule for MHC class II antigens, only recently was it demonstrated that fibroblasts transfected with a CDNA coding for CD4, and expressing high levels of this protein, bound tightly to human B cells bearing MHC-coded class II molecules. See for example, Guy et al., *Nature*, 328:626-629 (1987); Doyle et al., *Nature*, 330:258-259 (1987); and Sleckman et al., *Nature*, 328:351-353 (1987). This CD4-MHC Class II interaction was inhibited by either anti-CD4 or anti-MHC class II antibodies.

Several studies have provided evidence that the CD4 molecule acts as a receptor for the human immunodeficiency virus type 1 (HIV-1). For instance, Jameson et al., *Science.*, 240:1335-1338 (1988) reported that the binding site for HIV-1 on CD4 is probably formed by amino acid residues 16-49.

Other receptors of interest to the present invention are those which bind the constant (Fc) portion of immunoglobulin molecules. For instance, bacteria of several gram-positive species produce proteins which bind to the Fc region of Ig. For example see the best known of these Fc receptors is protein A of *Staphylococcus aureus*. Protein A has been widely used in laboratory and clinical diagnostic immunochemical procedures which exploit the ability to bind to a variety of immunoglobulin G (IgG) antibodies independently of antigen association.

The gene coding for protein A has been cloned, its CDNA sequence determined and its amino acid residue sequence deduced. See LöFdahl et al., *Proc. Natl. Acad. Sci. USA*, 80:697-701 (1983); Uhlén et al., *J. Biol. Chem.*, 259:1695-1702 (1984); and Moks et al., *Eur. J. Biochem.*, 156:637-643 (1986). In addition, those portions of protein A responsible for IgG-binding have been identified by Moks et al., *Eur. J. Biochem.*, 156:637-643 (1986), as consisting of five highly homologous segments, designated A-E, having sizes ranging from 50 (segment E) to 61 (segment D) amino acid residues.

Fc receptors with broader specificity than protein A are produced by Streptococcus species, especially those of Lancefield groups C and G. See for example, Björck et al., *J. Immunol.*, 133:969-974 (1984); Langone, I. I., *Adv. Immunol.*, 32:157-252 (1982); Myhre et al., *Infect. Immunol.*, 17:475-482 (1977); and Reis et al., *Mol. Immunol.*, 23:425-431 (1986). The protein produced by group G Streptococcus species known as protein G, has been shown to bind to all four classes of human IgG, including IgG3, to which protein A does not bind by Björck et al., *J. Immunol.*, 133:969-974 (1984). Furthermore, protein G binds more strongly than protein A to several animal IgG classes and mouse monoclonal antibodies as demonstrated by Akerströn et al., *J. Immunol.*, 135:2589-2592 (1985).

The gene for protein G has been cloned, its cDNA sequence determined and its amino acid residue sequence deduced. See Fahnestock et al., *J. Bact.*, 167:870-880 (1986). Like protein A, the structure of the IgG-binding regions of protein G have been determined by Guss et al., *EMBO J.*, 5:1567-1575 (1986). Those regions, designated C1, C2 and C3, each contain 55 amino acid residues and are separated within the protein by two "spacers", designated D1 and D2 of 16 amino acid residues each.

BRIEF SUMMARY OF THE INVENTION

It has now been discovered that the CD4 receptor binds the immunoglobulin heavy chain variable region ($V_H$) in a non-immune manner, i.e., in an antigen-independent manner.

The present invention is based on the elucidation of the antigen-independent $V_H$-binding sites on the CD4 protein and the determination of the amino acid residue sequences of those portions of the CD4 protein to which $_vH$ molecules bind. It is believed that at least three $V_H$-binding sites exist on the CD4 molecule, one located in the region of CD4 amino acid residues 30 to 40, another in the region formed by CD4 amino acid residues 60 to 90, and a third in the region of CD4 amino acid residues 130 to 160. Within the region of CD4 defined by residues 30-40, the sequence of amino acid residues represented by the formula:

-Ile-Lys-Ile-Leu- (CD4 residues 34 to 37) appears to play a particularly important role in antigen-independent Ig-binding. Furthermore, the results presented herein indicate that the region formed by CD4 amino acid 24 to 29 plays an important role in increasing the affinity of CD4 residues 34 to 37 for $V_H$.

Knowledge of these amino acid residue sequences has enabled the synthesis of polypeptides of the present invention which are capable of binding $V_H$ molecules, thereby allowing for their location and/or separation. As is readily apparent, these polypeptides can be used to isolate $V_H$ molecules from complex mixtures of proteins or for removing all or a portion of the $V_H$ molecules from a complex mixture of proteins. The subject polypeptides bind $V_H$ molecules when the $V_H$ molecules are present in the immunologically bound as well as free forms. That is, the subject polypeptides bind to immune complexes and can be used to identify the presence of such complexes or to isolate those complexes.

In addition, it has also been discovered that operatively linking a $V_H$-binding polypeptide of the present invention to a $V_H$ molecule increases the affinity of the $V_H$ molecule for its antigen, or, in the case of a catalytic $V_H$ molecule, the $V_H$ molecule substrate turn-over rate.

BRIEF DESCRIPTION OF THE DRAWINGS

In the drawings forming a portion of the specification:

FIGS. 1A-1 and 1A-2 illustrate the amino acid residue sequence of the CD4 molecule and a nucleotide sequence coding for it. The sequences are those described by Maddon et al., Cell, 42:93-104 (1985), as modified by Littman et al., Cell, 55:591 (1988). See Bialy, Biotech., 6:1268 (1988) for a further explanation of the modification and the reasons therefor.

FIGS. 2A-1 and 2A-2 illustrate a gene coding for a Staphylococcal Protein A and its deduced amino acid residue sequence as discussed by Uhlen et al., J. Biol. Chem., 259:1695-1702 (1984). FIG. 2B illustrates the amino acid residue sequences of preferred Protein A $F_C$-binding segments and nucleotide sequences coding for those segments. E, D, A, B and C are the different $F_C$-binding domains of staphyloccal Protein A; Z is the synthetic $F_C$-binding domain described in Nilsson et al., Protein Eng., 1:107-113 (1987). Amino acid differences are shown. An asterisk (*) represents a silent mutation, i.e. a change in the DNA sequence that does not alter the amino acid sequence coded for. A hyphen (-) represents the same DNA codon that is present in the Z domain. The underlined amino acids in the Z sequence are involved in the binding to Fc as described in Moks et al., Eur. J. Biochem., 156:637-643 (1986). The amino acids forming two x-helices are boxed.

FIGS. 3A-1 and 3A-2 illustrate a gene coding for a streptococcal Protein G and its deduced amino acid residue sequence as described by Guss et al., EMBO J., 5:1567-1575 (1986). FIG. 3B illustrates the base sequences and amino acid residue sequences encoded thereby of preferred Protein G $F_C$-binding segments. The identical DNA codons are indicated with a hyphen (-) and silent DNA codon changes are indicated with an asterisk (*).

In FIG. 4, antibodies not immunospecific for peptide p21-49 were examined at two concentrations (40 ug/ml and 4 ug/ml) for their ability to be bound by p21-49 in an antigen-independent manner. In each panel, the amount of binding is indicated by the optical density, which increases with greater binding.

In FIG. 5, the inhibition of monoclonal antibody binding to solid-phase peptide p21-49 by liquid-phase (soluble) peptide p21-49 is shown. In addition, the apparent binding constants of each monoclonal antibody, determined according to the method of Nieto et al., Mol.Immunol., 21:537 (1984).

FIG. 6A illustrates the enhancement of antibody binding to $V_H$-binding peptide p21-49, by the binding of antigen to antibody as evidenced by increasing optical density with in increasing antigen (Tg) concentration.

FIG. 6B illustrates peptide p21-49 does not inhibit the binding of antibody to antigen (antithyroglobulin to thyroglobulin) as evidenced by the approminately equivalent optical density observed at each peptide concentration.

In FIG. 7, the inhibition of $V_H$-binding peptide p21-49 binding to immunoglobulin in the presence of various concentrations of dextran sulfate is illustrated. The monoclonal antibodies used were 62, immunospecific for thyroglobulin and OKT4A, immunospecific for native CD4.

In FIG. 10, a preferred double stranded synthetic DNA sequence (gene) coding for $V_H$-binding peptide p21-49 is illustrated. The sequence coding for $V_H$-binding peptide p21-49 is flanked by Bam HI restriction endonuclease sites to allow this sequence to be easily inserted into the pRIT5 vector.

In FIG. 12, a preferred synthetic DNA sequence (gene) coding for the $F_C$-binding portion of streptococcal Protein G is shown. The synthetic DNA gene coding for the Protein G $F_C$-binding region is flanked by Eco RI restriction endonuclease sites to allow this sequence to be easily inserted into the PASI vector.

In FIG. 13, a preferred synthetic double stranded DNA sequence (gene) coding for the streptococcal Protein G $F_C$-binding region is shown. The synthetic gene coding for the Protein G $F_C$-binding region is flanked by DNA sequences compatible with Bam HI restriction endonuclease sites.

DETAILED DESCRIPTION OF THE INVENTION

A. Definitions

Figure 4B:
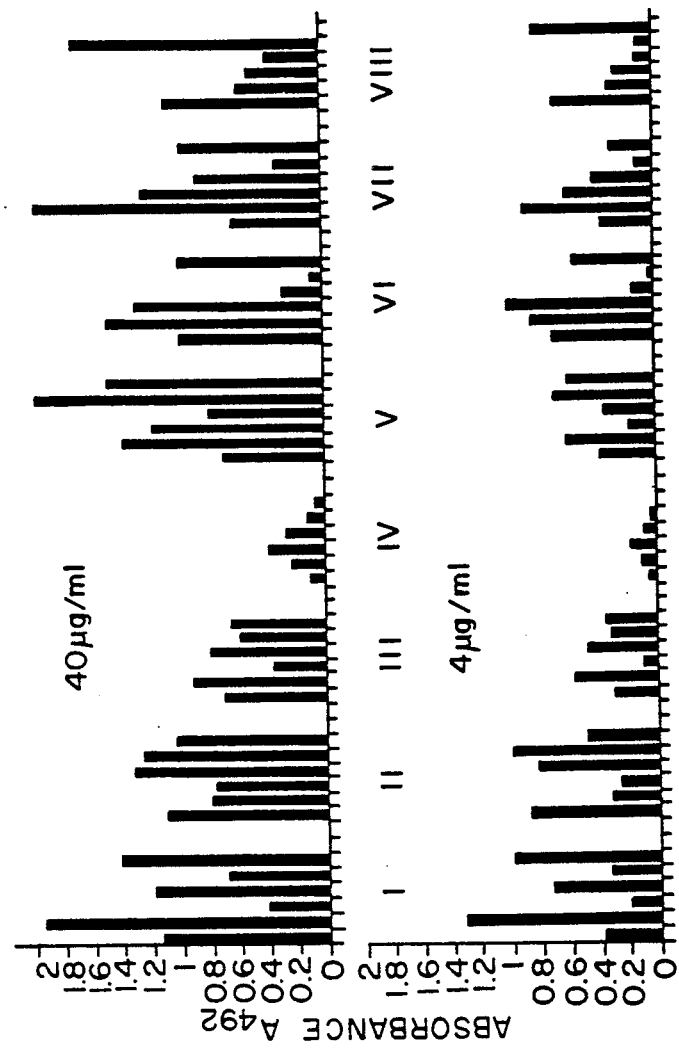
FIG. 4B illustrates the binding of $V_H$-binding peptide p21-49 to 47 human myeloma proteins of different isotypes (groups I-VIII).

Amino Acid Residue: The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptide. COOH refers to the free carboxy group present at the carboxy terminus of a polypeptide. A hyphen at the amino- or carboxy-terminus of a sequence indicates the presence of a further sequence of amino acid residues or a respective NH2 or COOH terminal group. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

Polypeptide: refers to a linear series of amino acid residues connected to one another by peptide bonds between the alpha-amino groups and carboxy groups of contiguous amino acid residues.

Peptide: as used herein refers to a linear series of not more than about 50 amino acid residues connected one to the other as in a polypeptide.

Protein: refers to a linear series of greater than 50 amino acid residues connected one to the other as in a peptide.

Synthetic peptide: refers to a chemically produced chain of amino acid residues linked together by peptide bonds that is free of naturally occurring proteins and fragments thereof.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleosides is typically referred to herein as a "nucleotide sequence", and is represented herein by a formula whose left to right orientation is in the conventional direction of 5' terminus to 3' terminus.

Immunoglobulin: refers to intact immunoglobulin molecules and immunologically active portions (capable of binding antigens) of immunoglobulin molecules. Exemplary imunoglobulin molecules are those portions of intact antibody molecules known in the art as $V_H$, Fab, Fab¹, F(ab¹)₂ and F(v).

B. Polypeptides

In one embodiment, a $V_H$-binding polypeptide of the present invention has an amino acid residue sequence corresponding to a portion of the sequence of the CD4 molecule, exhibits antigen-independent affinity for the $V_H$ region of Ig molecules, and is substantially, free from the ability to bind the human immunodeficiency virus, e.g., HIV-1 and/or HIV-2. Methods for determining the ability of a CD4-related polypeptide to bind HIV are well known in the art and typically involve examining the ability of a polypeptide to inhibit HIV-induced cell fusion (syncytium formation). See, for example, Jameson, et al., *Science*, 240:1335–1338 (1988). (The references cited herein are hereby incorporated by reference.)

Preferred polypeptides are those having an amino acid residue sequence corresponding, and preferably identical, to a sequence shown in Table 1.

TABLE 1

| Peptide | Amino Acid Residue Sequence |
|---|---|
| p 16–38 | NH₂—Cys—Thr—Ala—Ser—Gln—Lys—Lys—Ser—Ile—Gln—Phe—His—Trp—Lys—Asn—Ser—Asn—Gln—Ile—Lys—Ile—Leu—Gly—COOH |
| p 21–38 | NH₂—Lys—Lys—Ser—Ile—Gln—Phe—His—Trp—Lys—Asn—Ser—Asn—Gln—Ile—Lys—Ile—Leu—Gly—COOH |
| p 22–38 | NH₂—Lys—Ser—Ile—Gln—Phe—His—Trp—Lys—Asn—Ser—Asn—Gln—Ile—Lys—Ile—Leu—Gly—COOH |
| p 23–38 | NH₂—Ser—Ile—Gln—Phe—His—Trp—Lys—Asn—Ser—Asn—Gln—Ile—Lys—Ile—Leu—Gly—COOH |
| p 24–38 | NH—Ile—Gln—Phe—His—Trp—Lys—Asn—Ser—Asn—Gln—Ile—Lys—Ile—Leu—Gly—COOH |
| p 21–37 | NH₂—Lys—Lys—Ser—Ile—Gln—Phe—His—Trp—Lys—Asn—Ser—Asn—Gln—Ile—Lys—Ile—Leu—COOH |

A subject polypeptide includes any analog, fragment or chemical derivative of a polypeptide whose amino acid residue sequence is shown herein so long as the polypeptide is capable of binding Ig in an antigen-independent manner, i.e., as a nonantigenic ligand. Therefore, a present polypeptide can be subject to various changes, substitutions, insertions, and deletions where such changes provide for certain advantages in their use.

The term "analog" refers to any polypeptide having an amino acid residue sequence substantially identical to a sequence specifically shown herein conservatively substituted with a functionally similar residue. Examples of conservative substitutions include the substitution of one nonpolar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite binding activity is maintained.

The term "fragment" refers to any subject polypeptide having an amino acid residue sequence shorter than that of a polypeptide whose amino acid residue sequence is shown herein.

A subject polypeptide can be prepared using the solid-phase synthetic technique initially described by Merrifield, in J. Am. Chem. Soc. 85:2149-2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104-237, Academic Press, New York, N.Y. (1976). Appropriate protective groups for use in such syntheses will be found in the above texts as well as in J. F. W. McOmie, *Protective Groups in organic chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

The polypeptides of the present invention generally contain a $V_H$-binding segment of at least 10 amino acid residues and up to fifty amino acid residues, preferably 10-35 amino acid residues. The polypeptides can be linked to an additional sequence of amino acids at either or both the N-terminus and C-terminus, wherein the additional sequences are from 1-100 amino acids in length. Such additional amino acid sequences, or linker sequences, are heterologous to the CD4 amino acid residue sequence and can be conveniently affixed to a detectable label, solid matrix, or carrier. Labels, solid matrices and carriers that can be used with peptides of the present invention are described below. Typical amino acid residues used for linking are tyrosine, cysteine, lysine, glutamic acid and aspartic acid, or the like.

Any polypeptide of the present invention, including a chimeric polypeptide as described hereinbelow, may be used in the form of a pharmaceutically acceptable salt. Suitable acids which are capable of forming salts with the polypeptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

The present invention further includes a composition that includes a subject polypeptide in combination with one or more of a pH buffering agent, wetting agent, anti-oxidant, reducing agent, aqueous medium, and the like, such composition being formulated as an aqueous solution for a use as described herein or as a dry composition, such as a powder, that can be reconstituted to form an aqueous solution.

C. Chimeric Polypeptides

Another $V_H$-binding polypeptide of this invention is a chimeric polypeptide comprising at least one first segment and at least one second segment operatively linked by a peptide bond to form a single (unitary) polypeptide chain. The first segment is a $V_H$-binding segment having an amino acid residue sequence corresponding to all or a $V_H$-binding portion of a CD4 molecule. Preferred $V_H$-binding segments have an amino acid residue sequence corresponding, and preferably identical to, a sequence shown in FIG. 1 from about residue 30 to about residue 40, from about residue 21 to about residue 26, from about residue 35 to about residue 38, from about residue 21 to about residue 49, from about residue 16 to about residue 49, from about residue 16 to about residue 38, from about residue 21 to about residue 38, from about residue 22 to about residue 38, from about residue 21 to about residue 38, from about residue 23 to about residue 38, from about residue 24 to about residue 38, from about residue 29 to about residue 43, from about residue 32 to about residue 54, from about residue 38 to about residue 62, from about residue 58 to about residue 82, from about residue 66 to about residue 90, and from about residue 128 to about residue 161.

Also preferred are chimeric polypeptides having one or more $V_H$-binding segments of about 50 residues or less, typically about 15 residues to about 35 residues, wherein said segments have an amino acid residue sequence that corresponds, and is preferably identical, to a $V_H$-binding portion of CD4, and wherein each $V_H$-binding segment includes the amino acid residue sequence -Lys-Lys-Ser-Ile-Gln-Phe- and/or -Lys-Ileu-Leu-Gly-.

Preferably, the second segment is at least about 5, preferably at least about 15 and more preferably at least about 25, amino acid residues having a sequence that is heterologous to the sequence of CD4. A heterologous CD4 amino acid residue sequence is a sequence that does not immunologically cross-react with CD4. In preferred embodiments, the second segment of a subject chimeric polypeptide is comprised of a sequence of amino acid residues capable of binding the F, portion of an Ig molecule, i.e. , is an $F_C$-binding segment.

The $F_C$-binding segment of a subject chimeric polypeptide has an amino acid residue sequence corresponding to all or a $F_C$-binding portion of an $F_C$-binding protein. $F_C$-binding proteins are well known in the art. See, for example, Kronvall, J. *Immunol.,* 111:1401-1406 (1973); Shea, et al., *Infect. Immunol.,* 34:851-855 (1981); Langone, *Adv. Immunol.,* 32:157-252 (1982); Reis, et al., *J. Immunol.,* 132:3091 (1984); Reis, et al., *J. Immunol.,* 132:3098-3102 (1984); Bjorck, et al., *J. Immunol.,* 133:969-974 (1984); Akerstrom, et al., *J. Immunol.,* 135:2589-2592 (1985); and Myhre, et al., *Infect Immun.,* 17:475-482 (1977). Methods for cloning the genes coding for the proteins described in the above articles, sequencing those genes and deducing the amino acid residue sequence of the entire protein as well as the Ig-binding segments thereof, are well known in the art as discussed hereinbelow.

Particularly preferred $F_C$-binding proteins, all or a $F_C$-binding portion of which can be used to form a subject chimeric polypeptide, are those known in the art as Proteins A, Protein G and Protein Z. The amino acid residue sequences of Proteins A and Z, as well as DNA sequences coding for those proteins, are described in Lofdahl, et al., *Proc. Natl. Acad. Sci. USA.,* 80:697-701 (1983) and Nilsson, et al., *Prot. Eng.,* 1:107113 (1987). The amino acid residue sequence of Protein G, as well as a DNA sequence coding for that protein, are described in Moks, et al., *Eur. J. Biochem.,* 156:637-643 (1986); Guss et al., *EMBO,* 5:1567-1575 (1986); Gahnestock, et al., *J. Bact.,* 167:870-880 (1986); and Bjorck, et al., *Mol. Immunol.,* 24:1113-1122 (1987).

Particularly preferred $F_C$-binding segments useful in forming a subject chimeric polypeptide have an amino acid residue sequence corresponding, and more preferably identical, to at least a 10 amino acid residue portion of a sequence shown in Table 2.

TABLE 2

| Peptide | Amino Acid Residue Sequence |
|---|---|
| (A)[1] | —Thr—Tyr—Lys—Leu—Ile—Leu—Asn—Gly—Lys—Thr—Leu—Lys—Gly—Glu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—Lys—Pro—Glu—Val—Ile—Asp—, |
| (B)[1] | —Thr—Tyr—Lys—Leu—Ile—Leu—Asn—Gly—Lys—Thr—Leu—Lys—Gly—Glu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—, |
| (C)[2] | —Thr—Tyr—Lys—Leu—Val—Ile—Asn—Gly—Lys—Thr—Leu—Lys—Gly—Glu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—Lys—Pro—Glu—Val—Ile—Asp—, |
| (D)[2] | —Thr—Tyr—Lys—Leu—Val—Ile—Asn—Gly—Lys—Thr—Leu—Lys—Gly—GLu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—, |
| (E)[3] | —Thr—Lys—Leu—Val—Ile—Asn—Gly—Lys—Thr—Leu—Lys—Gly—Glu—Thr—Thr—Thr—Lys—Ala—Val—Asp—Ala—Glu—Thr—Ala—Glu—Lys—Ala—Phe—Lys—Gln—Tyr—Ala—Asn—Asp—Asn—Gly—Val—Asp—Gly—Val—Trp—Thr—Tyr—Asp—Asp—Ala—Thr—Lys—Thr—Phe—Thr—Val—Thr—Glu—Lys—Pro—Glu—Val—Ile—Asp—, |
| (F)[3] | —Thr—Try—Lys—Leu—Val—Ile—Asn—Gly—Lys—Thr—Leu—Lys—Gly—Glu—Thr—Thr—Thr—Lys—Ala—Val—Asp—Ala—Glu—Thr—Ala—Glu—Lys—Ala—Phe—Lys—Gln—Tyr—Ala— |

TABLE 2-continued

| Peptide | Amino Acid Residue Sequence |
|---|---|
| (G)[4] | Asp—Asp—Ala—Thr—Lys—Thr—Phe—Thr—Val—Thr—Glu—, —Leu—Lys—Gly—Glu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—Lys—Pro—Glu—Val—Ile—Asp—, |
| (H)[4] | —Leu—Lys—Gly—Glu—Thr—Thr—Thr—Glu—Ala—Val—Asp—Ala—Ala—Thr—Ala—Glu—Lys—Val—Phe—Lys—Gln—Tyr—Ala—Asn—Asp—Asn—Gly—Val—Asp—Gly—Glu—Trp—Thr—Tyr—Asp—Asp—Ala—Thr—Lys—Thr—Phe—Thr—Val—Thr—Glu—, |
| (I)[5] | —Val—Asp—Asn—Lys—Phe—Asn—Lys—Glu—Gln—Gln—Asn—Ala—Phe—Tyr—Glu—Ile—Leu—His—Leu—Pro—Asn—Leu—Asn—Glu—Glu—Gln—Arg—Asn—Ala—Phe—Ile—Gln—Ser—Leu—Lys—Asp—Asp—Pro—Ser—Gln—Ser—Ala—Asn—Leu—Leu—Ala—Glu—Ala—Lys—Lys—Leu—Asn—Asp—Ala—Gln—Ala—Pro—Lys—, |
| (J)[6] | —Ala—Gln—His—Asp—Glu—Ala—Gln—Gln—Asn—Ala—Phe—Tyr—Gln—Val—Leu—Asn—Met—Pro—Asn—Leu—Ala—Asp—Glu—Gln—Arg—Asn—Gly—Phe—Ile—Gln—Ser—Leu—Lys—Asp—Asp—Pro—Ser—Gln—Ser—Ala—Asn—Val—Leu—Gly—Glu—Ala—Gln—Lys—Leu—Asn—Asp—Ser—Gln—Ala—Pro—Lys—, |
| (K)[7] | —Ala—Asp—Asn—Asn—Phe—Asn—Lys—Asp—Gln—Gln—Ser—Ala—Phe—Tyr—Glu—Ile—Leu—Asn—Met—Pro—Asn—Leu—Asn—Glu—Ala—Gln—Arg—Asn—Gly—Phe—Ile—Gln—Ser—Leu—Lys—Asp—Asp—Pro—Ser—Gln—Ser—Thr—Asn—Val—Leu—Gly—Glu—Ala—Lys—Lys—Leu—Asn—Glu—Ser—Gln—Ala—Pro—Lys—, |
| (L)[8] | —Ala—Asp—Asn—Asn—Phe—Asn—Lys—Glu—Gln—Gln—Asn—Ala—Phe—Tyr—Glu—Ile—Leu—Asn—Met—Pro—Asn—Leu—Asn—Glu—Glu—Gln—Arg—Asn—Gly—Phe—Ile—Gln—Ser— —Ala—Asp—Asn—Asn—Phe—Asn—Lys—Glu—Gln—Gln—Asn—Ala—Phe—Tyr—Glu—Ile—Leu—Asn—Met—Pro—Asn—Leu—Asn—Glu—Glu—Gln—Arg—Asn—Gly—Phe—Ile—Gln—Ser—Leu—Lys—Asp—Asp—Pro—Ser—Gln—Ser—Ala—Asn—Leu—Leu—Ser—Glu—Ala—Lys—Lys—Leu—Asn—Glu—Ser—Gln—Ala—Pro—Lys—, |
| (M)[9] | —Ala—Asp—Asn—Lys—Phe—Asn—Lys—Glu—Gln—Gln—Asn—Ala—Phe—Tyr—Glu—Ile—Leu—His—Leu—Pro—Asn—Leu—Asn—Glu—Glu—Gln—Arg—Asn—Gly—Phe—Ile—Gln—Ser—Leu—Lys—Asp—Asp—Pro—Ser—Gln—Ser—Ala—Asn—Leu—Leu—Ala—Glu—Ala—Lys—Lys—Leu—Asn—Asp—Ala—Gln—Ala—Pro—Lys—, and |
| (N)[10] | —Ala—Asp—Asn—Lys—Phe—Asn—Lys—Glu—Gln—Gln—Asn—Ala—Phe—Tyr—Glu—Ile—Leu—His—Leu—Pro—Asn—Leu—Thr—Glu—Glu—Gln—Arg—Asn—Gly—Phe—Ile—Gln—Ser—Leu—Lys—Asp—Asp—Pro—Ser—Val—Ser—Lys—Glu—Ile—Leu—Ala—Glu—Ala—Lys—Lys—Leu—Asn—Asp—Ala—Gln—Ala—Pro—Lys—, |

[1] The amino acid sequence of Streptococcal Protein G region C1 described in Guss, et al., EMBO J., 5:1567–1575 (1986).
[2] The amino acid sequence of Streptococcal Protein G region C2 described in Guss, et al., EMBO J., 5:1567–1575 (1986).
[3] The amino acid sequence of Streptococcal Protein G region C3 described in Guss, et al., EMBO J., 5:1567–1575 (1986).
[4] The amino acid sequence coded by the Cla I restriction enzyme fragment described in FIG. 4 of Guss, et al., EMBO J., 5:1567–1575 (1986).
[5] The amino acid sequence of the Z protein described in Nilsson, et al., Protein Eng., 1:107–113 (1987).
[6] The amino acid sequence of the E domain of Staphylococcal Protein A described in Nilsson, et al., Protein Eng., 1:107–113 (1987).
[7] The amino acid sequence of the D domain of Staphylococcal Protein A described in Nilsson, et al., Protein Eng., 1:107–113 (1987).
[8] The amino acid sequence of the A domain of Staphylococcal Protein A described in Nilsson, et al., Protein Eng., 1:107–113 (1987).
[9] The amino acid sequence of the B domain of Staphylococcal Protein A described in Nilsson, et al., Protein Eng., 1:107–113 (1987).
[10] The amino acid sequence of the C domain of Staphylococcal Protein A described in Nilsson, et al., Protein Eng., 1:107–113 (1987).

The antigen-dependent Ig-binding segments (i.e., the $V_H$-binding and $F_C$-binding segments) of a subject chimeric polypeptide can be either contiguous or adjacent to each other within the polypeptide chain. Where they are adjacent, the segments are separated by amino acid residues forming a spacer segment typically comprised of from about 5 conveniently up to about 50 residues, preferably about 15 to about 30 residues as are found in Protein A and Protein G. A subject chimeric polypeptide can contain a plurality of the same or different $V_H$-binding and $F_C$-binding segments. Where three or more of the Ig-binding segments are adjacent within a subject chimeric polypeptide, the spacer segments can be the same or different. It is preferred that the amino acid residue sequence of a spacer segment correspond to at least a portion of the sequence of a spacer segment present in a naturally occurring $F_C$-binding protein, such as Protein A or Protein G. A spacer segment can also be comprised of a sequence of residue corresponding to a portion of the CD4 sequence that is contiguous to one of the $V_H$-binding regions of CD4 as described herein.

A subject chimeric polypeptide can further contain a head and/or tail segment of 1 conveniently up to about 50, such as about 5 orout 10, typically about 15 or about 30, at its amino- or carboxy terminus, respectively, where such a segment is advantageous in the polypeptide's making or use. For instance, a tail segment can provide a means for linking the subject chimeric polypeptide to a solid matrix, where as a leader segment can advantageously be used to facilitate secretion of the polypeptide during its expression in cells. It is preferred that the amino acid residue sequence of a head or tail segment found in Protein A or Protein G. A head or tail segment can also be comprised of a sequence of residues corresponding to a portion of the CD4 sequence that is contiguous to one of the $V_H$-binding regions of CD4 as described herein.

D. DNA and Recombinant DNA Molecules

In living organisms, the amino acid residue sequence of a protein or polypeptide is directly related via the genetic code to the deoxyribonucleic acid (DNA) sequence of the gene that codes for the protein. Thus, a gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

Figure 2B:
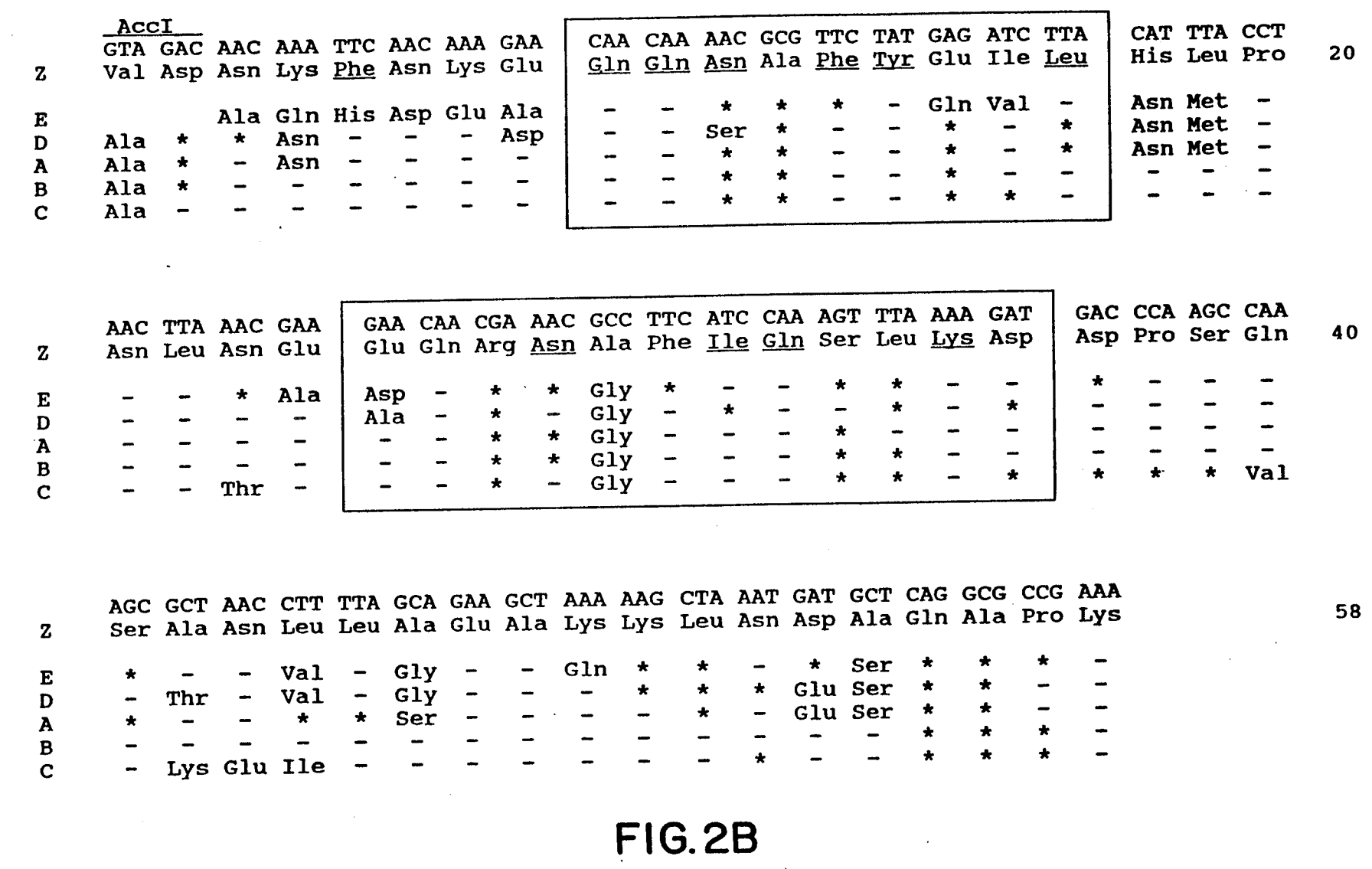

The present invention contemplates a deoxyribonucleic acid (DNA) molecule or segment that defines a gene coding for, i.e., capable of expressing, a subject chimeric polypeptide. Preferred DNA molecules code for chimeric polypeptides having a $V_H$-binding segment whose amino acid residue sequence corresponds to a sequence shown in Tables 1 and 4. Preferred DNA molecules also include those coding for a $F_C$-binding segment whose amino acid residue sequence corresponds, and is preferably identical, to a sequence shown in Table 2. DNA molecules containing $V_H$-binding or $F_C$-binding segment-coding nucleotide sequences corresponding to all or a portion of those shown in FIGS. 1-3 are most preferred.

DNA molecules that encode the subject proteins can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA molecules including base sequences identical to all or a portion of those shown in FIGS. 1-3 are preferred.

A DNA molecule that includes a DNA sequence encoding a subject polypeptide can be prepared by operatively linking (ligating) appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA molecules.

The present invention further contemplates a recombinant DNA molecule comprising a vector operatively linked, for replication and/or expression, to a subject DNA molecule, i.e., a DNA molecule defining a gene coding for a subject chimeric polypeptide.

As used herein, the term "vector" refers to a DNA molecule capable of autonomous replication in a cell and to which another DNA segment can be operatively linked so as to bring about replication of the attached segment. Vectors capable of directing the expression of a gene delivered by a subject DNA segment are referred to herein as "expression vectors". Thus, a recombinant DNA molecule (RDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the subject chimeric polypeptide gene included in DNA segments to which it is operatively linked.

In preferred embodiments, a vector contemplated by the present invention includes a procaryotic relicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the subject chimeric polypeptide gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUCs, pUCs, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327-341 (1982).

The use of retroviral expression vectors to form the rDNAa of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge, et al., *Mol. Cell. Biol.*, 4:1730-37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase of *E. coli* DNA polymerase I, enzymes that remove protruding, 3', single-stranded termini with their 3'-5' exonucleotytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophase T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

The present invention also relates to a host cell transformed with a recombinant DNA molecule of the present invention preferably an RDNA capable of expressing a subject chimeric polypeptide. The host cell can be either procaryotic or eucaryotic. Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Clonin A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730-37 (1984); Graham et al., *Virol.*, 52:456 (1973); and Wigler et al., *Proc. Natl. Acad. Sci. USA*, 76:1373-76 (1979).

Successfully transformed cells, i.e., cells that contain a recombinant DNA molecule of the present invention, can be identified by well known techniques. For example, cells resulting from the introduction of an RDNA of the present invention can be cloned to produce monoclonal colonies. Cells from those colonies can be harvested, lysed and their DNA content examined for the presence of the RDNA using a method such as that described by Southern, *J. Mol. Biol.*, 98-503 (1975) or Berent et al., *Biotech.*, 3:208 (1985).

In addition to directly assaying for the presence of RDNA, successful transformation can be confirmed by well known immunological methods when the RDNA is capable of directing the expression of a subject chimeric polypeptide. For example, cells successfully transformed with an expression vector produce proteins displaying CD4 $V_H$-binding region antigenicity. Samples of cells suspected of being transformed are harvested and assayed for the presence of CD4 $V_H$-binding region antigenicity using antipolypeptide antibodies specific for that region.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying antigen independent $V_H$-binding activity.

Nutrient media useful for culturing transformed host cells are well known in the art and can be obtained from several commercial sources. In embodiments wherein the host cell is mammalian, a "serum-free" medium is preferably used.

E. Compositions and Polypeptides Linked to Labels and Solid Matricies

The present invention further contemplates a composition containing, in admixture, a $V_H$-binding polypeptide, preferably a $V_H$-binding polypeptide having an amino acid residue sequence shown in Tables 1 and 3, and a $F_c$-binding polypeptide, preferably a $F_c$-binding polypeptide having an amino acid residue sequence corresponding to that of Protein A, Protein G, Protein Z and/or Table 2. Preferred combinations include one or more of p16-49, p21-49, p16-38 and p21-38 with one or more of Protein A, Protein G and Protein Z.

Typically, subject composition has a $V_H$-binding polypeptide to $F_c$-binding polypeptide molar ration in the range of about 1:10 to about 10:1, preferable about 1:5 to about 5:1, and more preferably about 1:1. The admixed polypeptides can be in the form of a powder or solution. Solutions of $V_H$-binding and $F_c$-binding polypeptides typically have a pH value range of about 5 to about 9 and an ionic strength of no more than that equivalent to about one molar sodium chloride.

The $V_H$-binding polypeptides of the present invention, including the before described chimeras, can be linked to a label to form a labeled probe. Preferred labels include alkaline phosphatase [O'Sullivan et al., *FEBS Letters*, 95:311 (1978)], biotin, horse radish peroxidase, dichlorotriazinylaminofluorescein [DTAF; Blakeslee et al., *J. Immunol. Meth.*, 13:320 (1977)], ferritin (Carlsson et al, *Biochem. J.*, 173:723 (1978)], fluoroscene isothiocyanste [FITC; McKinney et al., *Anal. Biochem*, 14:421 (1966)], beta-galactosidase [Ishikawa et al., *Scand. J. Immunol.*, 8:43 (1978)], sulforhodamine 101 acid chloride (Texas Red), tetramethyrhodamine isothiocyanate [TRITC; Amante et al., *J. Immunol. Meth.*, 1:289 (1972)], gold [Horisberger et al., *Histochem.*, 82:219 (1985)], and the like.

A $V_H$-binding polypeptide of this invention can be linked to a solid matrix, i.e., a matrix substantially insoluble in aqueous solution, thereby forming an affinity sorbent useful in practicing the methods of this invention. Typical solid matrices include latex or acrylic beads, agarose, cellulose, SEPHAROSE (agarose beads) and the like. Preferably, the solid matrix is hydrophilic.

In view of the finding that complexes containing antibodies bound to a polypeptide of this invention display an increased affinity for antigen, such complexes in substantially isolated (substantially free of antigen-antibody immunoreaction products) form are contemplated herein. Preferred $V_H$-binding polypeptide-antibody molecule complexes are those containing a $V_H$-binding polypeptide having an amino acid residue sequence corresponding, and preferably identical to, a polypeptide shown in Table 4. Preferably, only one type of antibody molecule is present in the composition, i.e., a composition having the characteristics of a monoclonal antibody. The $V_H$-binding polypeptide is linked to the $V_H$ region of the antibody molecule at a site other than the antibody molecule's antigen-binding site. The complex is therefore capable of immunoreacting with antigen, or, in the case of catalytic antibody molecules (abzymes), binding substrate as part of an enzymatic reaction. The composition can take the form and be formulated as previously discussed for the subject polypeptides.

In another embodiment, the present invention contemplates a V.-binding conjugate comprised of a $V_H$-binding polypeptide of this invention operatively linked, preferably covalently, to an $F_c$-binding polypeptide, the linkage being by other than a peptide bond between the alpha-amino group and carboxy group of contiguous amino acid residues. In preferred conjugates, one or more of the peptides of Table 4 are coupled to Protein A, Protein G, Protein Z or an $F_c$-binding peptide of Table 2.

Also contemplated is a $_{V}H$-binding self-conjugate comprised of a plurality of $V_H$-binding polypeptides operatively linked, preferably covalently, to each other by other than a peptide bond between the alpha-amino group and carboxy group of contiguous amino acid residues. Preferred self-conjugates contain a $V_H$-binding peptide of Table 4. one type of self-conjugate is a homoconjugate wherein each of the plurality of linked peptides is substantially identical in amino acid residue sequence.

In preferred embodiments, the $V_H$-binding conjugates of this invention are in a composition substantially free of, or isolated from, non-conjugated (free) $V_H$-binding polypeptide so that of the total peptide present, less than about 5% by weight is in non-conjugated form of course, the conjugates and conjugate compositions of this invention can take the form and be formulated as previously discussed for the subject polypeptides.

F. Methods

The affinity of the subject $V_H$-binding polypeptides for Ig can advantageously be used in any method similar to that reported for Protein A, Protein G or Protein Z. Particularly preferred is a method for separating Ig molecules, including $V_H$-containing portions of Ig molecules, from an aqueous composition containing a complex mixture of proteins and recovering the separated Ig molecule and/or Ig-depleted composition as a purified product. See, for example, U.S. Pat. Nos. 4,409,330, No. 4,464,165 and No. 4,687,734. Generally, the method utilizes the following steps.

(1) Admixing the Ig-containing ($V_H$-containing) aqueous sample with a subject polypeptide to form a binding reaction admixture. The Ig molecules can be present in the sample in free (nonimmunologically bound) form or in the form of immune complexes.

(2) Maintaining the binding reaction admixture under Ig-binding conditions for a time period, typically predetermined, sufficient for a portion of the Ig molecules present to bind the subject polypeptide, thereby forming a Ig-polypeptide complex and a non-bound sample portion. Maintenance time periods are typically in the range of about 10 minutes to about 16–20 hours under Ig-binding conditions.

"Ig-binding conditions" are those that maintain the biological activity of the polypeptide molecules of this invention and the antibodies sought to be bound, and include a temperature range of about 4 degrees C. to about 45 degrees C., a pH value range of about 5 to about 9 and an ionic strength of no more than that equivalent to about one molar of sodium chloride. Methods for optimizing such conditions are well known in the art.

(3) Segregating the complex from the non-bound sample portion and recovering the segregated complex as isolated Ig and/or recovering the segregated non-bound sample portion as Ig-depleted sample. Segregation of reactants from products is typically accomplished using a size separation technique, such as centrifugation, chromatography and the like, and/or washing, such as by dialyzing, with an aqueous solution, preferably a buffer, that does not significantly promote dissociation of the complex, of course, the Ig can also be separated and recovered from the segregated complex by adaptation of any of the techniques similarly used in the art for Protein A, Protein G and the like. Such methods typically involve exposing the complex to a destabilizing salt concentration (usually low relative to the Ig-binding condition used) and/or pH value (also usually low relative to the Ig-binding condition used). Competitive dissociation with an agent such as dextran sulfate can also be employed, typically followed by dialization to remove the competitive agent.

The affinity of the subject V.-binding polypeptides can also be used to assay for the presence of $V_H$ molecules, typically in the form of whole Ig and/or $V_H$-containing portions thereof, in a sample. The method involves admixing a sample suspected of containing $V_H$ molecules with a subject $V_H$-binding polypeptide. The binding reaction admixture so formed is maintained under Ig-binding conditions as previously described to permit complex formation between the subject $V_H$-binding polypeptide and any V. molecules present in the sample. The presence of any complex formed is then detected, and thereby the presence of $V_H$ molecules present in the sample.

Methods for detecting the presence and/or amount of the $V_H$-binding polypeptide-containing complex formed are well known and include those used in the art for detecting complexes containing Protein A and Protein G. A preferred method involves detecting the presence in the complex of a label that has been operatively linked to the subject $V_H$-binding polypeptide, either before or after complex formation.

The present invention further contemplates a method of increasing the affinity of an antibody for an antigen with which it immunoreacts. The method comprises forming a complex containing the antibody and a $V_H$-binding polypeptide of this invention, preferably a polypeptide consisting essentially of a $V_H$-binding fragment of CD4, and more preferably one or more of peptides shown in Table 4. The $V_H$-binding polypeptide can be covalently linked to the $V_H$, but the Method typically first involves forming a non-covalent complex via the previously discussed binding reaction.

EXAMPLES

The following examples illustrate but do not limit the present invention.
1. Peptide D16-49 of CD4 Binds to Murine Monoclonal Antibodies and Human Myeloma Proteins A. Polypeptides The polypeptides, whose amino acid residue sequences are shown in Tables 1 and 4, were synthesized using the classical solid-phase technique described by Merrifield, *Adv. Enzymol.*, 32:221-96 (1969) as adapted for use with a model 430A automated peptide synthesizer (Applied Biosystems, Foster City, Calif.). Polypeptide resins were cleaved by hydrogen fluoride, extracted and analyzed for purity by high-performance liquid chromatography (HPLC) using a reverse-phase C18 column manufactured by Waters Associates, Milford, Mass.

B. Peptide P21-49 Binds Murine and Human Antibodies.

The binding of peptide p21-49 to the mouse and human antibodies was examined by Enzyme-Linked Immuno-absorbent Assay (ELISA) in a manner similar to that described in *Antibodies A Laboratory Manual*, Harloe and Lane, Cold Spring Harbor Laboratory, N.Y., 1988. Briefly, solid-phase affixed p21-49 (a p21-49-containing solid support) was prepared by admixing 50 microliters (ul) of 0.9% sodium chloride (coating buffer) containing 5 to 10 micrograms (ug) per milliliter (ml) of the peptide to the wells of a polyvinyl or polystyrene microtiter plate. The plate was maintained for six hours at 37 degrees (37° C.) on a rotating platform to allow the peptide to adhere to the wells and form solid supports. After aspirating the excess liquid from the wells, 200 ul of washing solution containing TWEEN 20 (0.5% polyoxyethylenesorbitan monolaurate) in phosphate buffered saline (0.5M sodium chloride, 0.01M sodium phosphate at pH 7.2; PBS) was admixed to each well and immediately removed by aspiration. After aspirating the excess liquid from the wells 200 ul of blocking solution consisting of 1% bovine serum albumin (BSA) in phosphate buffered saline at pH 7.4 was admixed to each well, and the wells maintained at room temperature for one hour. The wells were washed with 200 ul a solution containing 0.5% TWEEN-20 (Polyoxyethylenesorbitan monolaurate) in PBS and the wash solution immediately removed by aspiration.

A first antibody, either a murine monoclonal antibody or a purified human myeloma protein was diluted to approximately 80 ug per ml in binding buffer consisting of 1% BSA and 0.5% TWEEN 20 (polyoxyethylenesorbitan monolaurate) in PBS and then various amounts, depending on the final antibody concentration desired, were admixed to each well and the wells maintained at room temperature for 3 or 4 hours in a humidified atmosphere. The wells were then washed 6 times with washing buffer and the excess liquid removed by aspiration.

50 ul of a horse radish peroxidase (HRP)-conjugated anti-mouse Ig secondary antibody (Cappel, Cochranvile, Pa.) or HRP-conjugated antihuman Ig (Sigma, St. Louis, Mo.) diluted 1:10,000 and 1:1,500, respectively, in binding buffer supplemented with 15% heat inactivated calf serum, was then admixed to each well. The wells were maintained for 1 hour at room temperature and then washed several times with washing buffer. 100 ul of freshly prepared substrate, prepared by adding 4 mg of 0-phenylendiamine and 4 ul of a 30% solution of hydrogen peroxide to 10 ml of a buffer containing 0.1M citric acid and 0.2M dibasic sodium phosphate at pH 5.0. were admixed to each well. The wells were then maintained (incubated) for 30 minutes at room temperature in the dark. The reaction was stopped by adding 25 ul per well of a stop buffer consisting of aqueous 4N $H_2SO_4$. The amount of colored reaction product produced was determined by measuring the absorbance at 492 nanometers (nm).

Figure 4A:
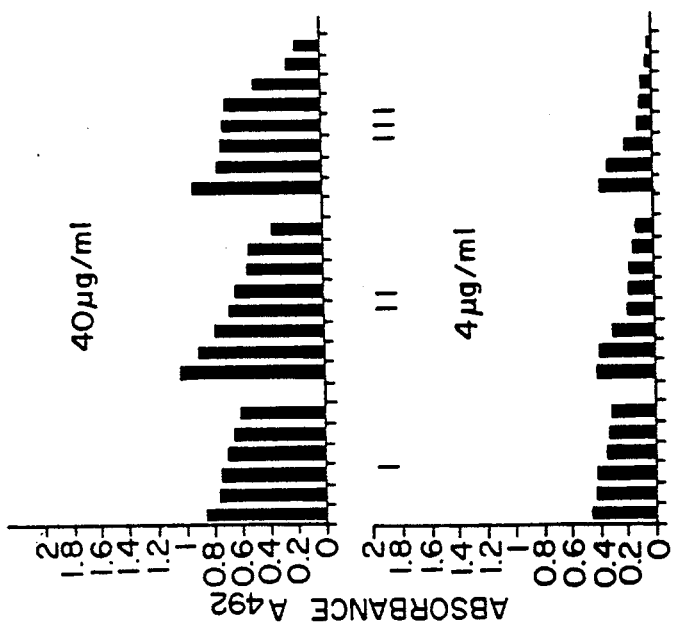
FIG. 4A illustrates the binding of $V_H$-binding peptide p21-49 to 22 murine monoclonal antibodies of different antigen specificities and isotypes (groups I, II and III).

The binding of peptide p21-49 to 22 murine monoclonal antibodies of different antigen specificities and isotypes (groups 1, II and III) is shown in FIG. 4A. Peptide p21-49 binds murine monoclonal antibodies immunospecific for 3 different antigens demonstrating that the peptide binds antibody regardless of that antibody's specificity.

The binding of peptide p21-49 to 36 human myeloma proteins of different isotypes is shown in FIG. 4B. Peptide p21-49 binds human myeloma proteins of 8 different isotypes demonstrating the peptide's isotype-independent antibody binding properties.

The isotype and specificity of each of the antibodies tested are listed in Table 3.

TABLE 3

| Antibody Group (Panel/#) | Antibody Isotype | Antibody Specificity |
|---|---|---|
| A/I | IgG$_1$,IgM | bovine thyroglobulin |
| A/II Factor | IgG r | human Von Willebraud |
| A/III | IgG,IgG$_{2b}$ | nitrophenyl acetyl |
| B/I | IgG$_1$ | human myeloma |
| B/II | IgG$_2$ | human myeloma |
| B/III | IgG$_3$ | human myeloma |
| B/IV | IgG$_4$ | human myeloma |
| B/V | IgM | human myeloma |
| B/VI | IgA | human myeloma |
| B/VII | IgD | human myeloma |
| B/VIII | IgE | human myeloma |

2. Peptide P21-49 Binds Specifically to Immunoglobulins.

The specificity of the binding interaction between peptide P21-49 and immunoglobulins was determined by inhibiting that interaction with liquid phase peptide p21-49. In addition to demonstrating the binding specificity of this peptide, the apparent binding constant was also determined. After the microtiter wells were coated with peptide P21-49 as described in Example 1B using peptide at a concentration of 20 ug/ml in coating buffer, peptide p21-49 was added to three replicate wells at a final concentration of 40 ug/ml, 20 ug/ml, 10 ug/ml, 5 ug/ml, 2.5 ug/ml, 1.25 ug/ml, 0.62 ug/ml and 0.31 ug/ml. An aliquot (25 ul) of HRP-conjugated murine monoclonal antibody, diluted to about 1 ug/ml in binding buffer, was then admixed to each well. The wells were maintained at room temperature for 3 or 4 hours in a humidified atmosphere. The wells were then washed 6 times with washing buffer and the excess liquid removed by aspiration. The amount of monoclonal antibody bound in each well was then determined as described in Example 1B.

Monoclonal antibody 62, monoclonal antibody 18.85, monoclonal antibody Q5/13 and monoclonal antibody 18.1.16 were studied in this fashion and the percent of maximal binding versus the peptide concentration was found to be about linear over the peptide concentration range examined for each MAb, as is shown in FIG. 5. The apparent binding constants in ml per gram are also shown for each of the monoclonal antibodies in FIG. 5. It should be noted that the binding constants, which were all in the range of $3-5 \times 10^5$ ml/g, are somewhat less than is typically observed for monoclonal antibody-antigen immunoreactions, which are typically on the order of $10^6-10^{12}$ ml/g.

3. Localization of the CD4 Region Containing the Immunoglobulin Binding Activity.

The region of CD4 that binds immunoglobulins was localized by synthesizing, according to Example 1A, the peptides shown in Table 4. Each peptide's ability to bind mouse monoclonal antibodies was determined using the ELISA assay described in Example 1B.

TABLE 4

CD4 PEPTIDES

| Ig Binding[1] | Designation[2] | SEQUENCE |
|---|---|---|
| 4+ | p 16-49 | CTASQ KKSIQ FHWKN SNQIK ILGNQ GSFLT KGPS |
| 4+ | p 21-49 | KKSIQ FHWKN SNQIK ILGNQ GSFLT KGPS |
| 3+ | p 16-38 | CTASQ KKSIQ FHWKN SNQIK ILG |
| 3+ | p 21-38 | KKSIQ FHWKN SNQIK ILG |
| * | p 21-37 | KKSIQ FHWKN SNQIK IL |
| * | p 21-36 | KKSIQ FHWKN SNQIK I |
| * | p 21-35 | KKSIQ FHWKN SNQIK |
| 0 | p 21-34 | KKSIQ FHWKN SNQI |
| * | p 21-33 | KKSIQ FHWKN SNQ |
| * | p 22-38 | KSIQ FHWKN SNQIK ILG |
| * | p 23-38 | SIQ FHWKN SNQIK ILG |
| * | p 24-38 | IQ FHWKN SNQIK ILG |
| 0 | p 21-29 | KKSIQ FHWK |
| 2+ | p 25-38 | Q FHWKN SNQIK ILG |
| 2+ | p 29-43 | KN SNQIK ILGNQ GSF |
| 1+ | p 32-54 | NQIK ILGNQ GSFLT KGPSK LNDR |
| 1+ | p 38-62 | GNQ GSFLT KGPSK LNDRA DSRRS LW |
| 0 | p 39-60 | NQ GSFLT KGPSK LNDRA DSRRS |
| 0 | p 42-49 | SFLT KGPS |
| 0 | p 48-72 | PSK LNDRA DSRRS LWDQG NFPLI IK |
| 1+ | p 58-82 | RRS LWDQG NFPLI IKNLK IEDSD TY |
| 1+ | p 66-90 | NFPLI IKNLK IEDSD TYICE YEDQK |
| 0+ | p 137-161 | NIQG GKTLS VSQLE LQDSG TWTCT Y |
| 1+ | p 128-161 | VQC RSPRG KNIQG GKTLS VSQLE LQDSG TWTCT Y |

Figure 15:
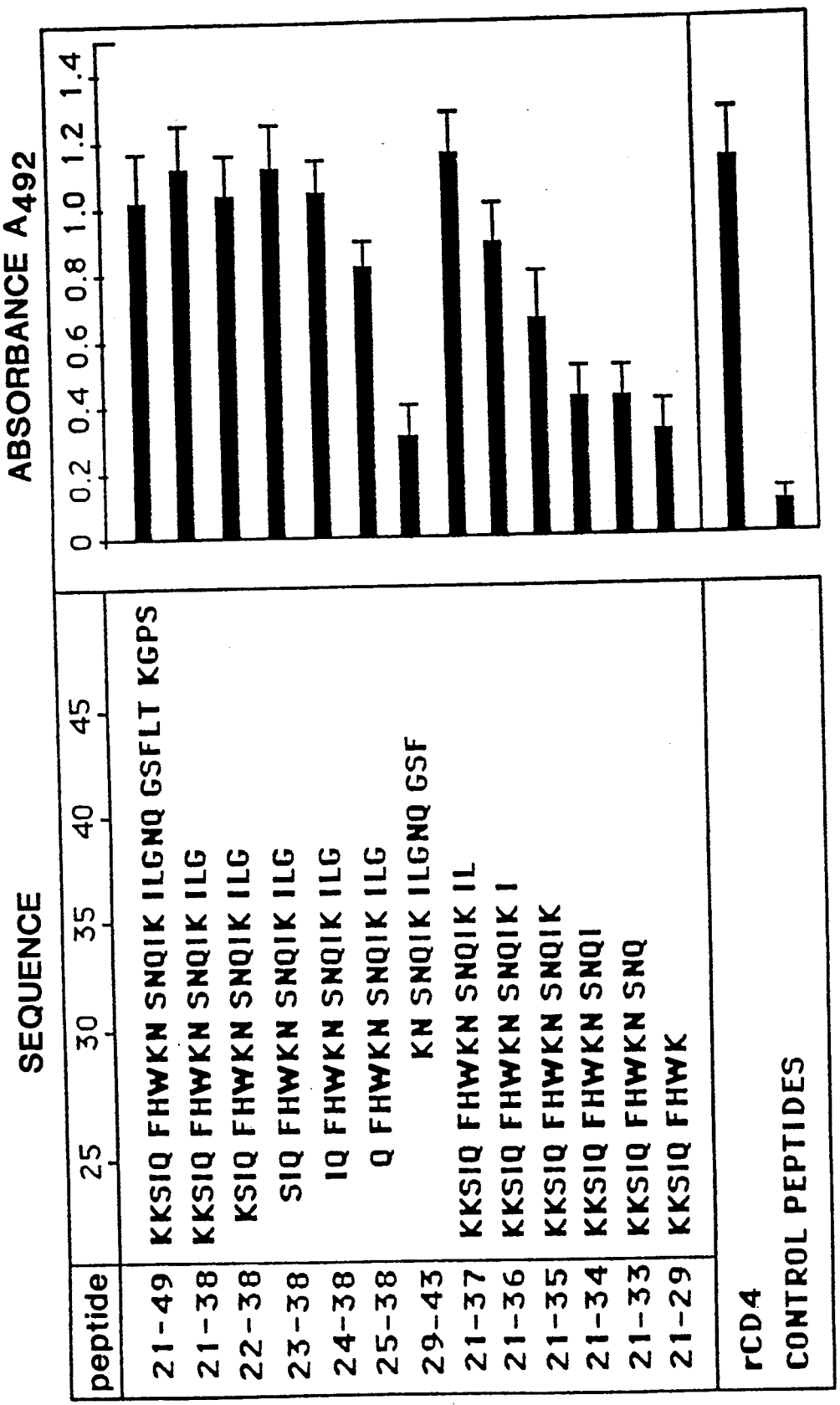
FIG. 15 reports the binding of various synthetic CD4 peptides spawning from amino acid residue 21 to 38 of the first extracellular domain of CD4. The binding of recombinant CD4 (rCD4) and p21-29 are shown as positive controls.

[1]The amount of antigen-independent immunoglobulin binding activity detected for each peptide is shown on a scale of 0 to 4+ with 0 being no substantial binding, 1+ being weak binding and 2+, 3+ and 4+ indicating increasing levels of significant binding.
[2]The designation given each peptide corresponds to the position of the peptide's sequence within the CD4 molecule as shown in FIG. 1.
*See FIG. 15 for relative binding affinity of this peptide.

The results shown in Table 4 and FIG. 15 indicate that the amino acid residue sequence IKIL, corresponding to residues 34-37 of CD4, appears to play an important role in the antigen-independent binding of polypeptide to $V_H$. Peptides p22-38, p23-38, p24-38 and p21-37 gave comparable binding with that of p21-38 and p21-49. Peptides 21-36 and 21-35 bound with the above background values.

4. Peptide P21-49 Exhibits Enhanced Binding to Antigen-Antibody Complexes

The effect of antigen binding on peptide p21-49 immunoglobulin binding was determined using monoclonal antibodies immunospecific for thyroglobulin. Briefly, p21-49 was affixed to the wells of microliter plates as described in Example 1B. Thyroglobulin was then admixed to the wells at a final concentration ranging from 0.005 mg/ml to 4 mg/ml. Monoclonal antibodies immunospecific for thyroglobulin were then admixed to the wells at a concentration of approximately 20 ug/ml in binding buffer consisting of 1% BSA and 0.5% Tween-20 in PBS and the wells maintained at room temperature for 4 hours in a humidified atmosphere to allow the antigen-antibody complexes to form and to be bound by the immobilized peptide. The wells were then washed 6 times with washing buffer and the excess liquid removed by aspiration. The assay was completed according to Example 1B.

At final concentrations of greater than 0.5 ug/ml, thyroglobulin enhanced the binding of the antibody to the p21-49 immobilized on the plate as shown in FIG. 6A. These results suggest that the binding of antigen by an antibody induces a conformational change in the antibody which in turn increases the affinity of the antibody for the $V_H$-binding polypeptide.

In a similar assay designed to show that $V_H$-binding polypeptides of this invention do not interfere with an antibody's ability to bind antigen, thyroglobulin was affixed to microtiter wells as described in Example 1B using 50 ul of coating buffer containing 2 ug/ml thyroglobulin. Peptide pl6-49 was then admixed to each well at a final concentration ranging from 0.015 ug/ml to 40 ug/ml. The anti-thyroglobulin murine monoclonal antibody, diluted to approximately 20 ug/ml in binding buffer consisting of 1% BSA and 0.5% Tween-20 in PBS, was admixed to each well and the wells maintained at room temperature for 4 hours in a humidified atmosphere. 200 ul of washing solution was admixed to each well and removed by aspiration and the remainder of the assay completed according to Example 1B.

Peptide pl6-49 did not interfere with antigen binding even at a concentration of 40 ug/ml as shown in FIG. 6B. Thus, the polypeptides of the present invention do not bind Ig at the Ig antigen binding site.

5. Binding of Peptide v21-49 to Immunoglobulins is Inhibited by Dextran Sulfate.

The binding of peptide p21-49 to various immunoglobulins was determined in the presence of varying concentration of dextran sulfate. Briefly, peptide p21-49 was affixed to the wells of microliter plates as described in Example 1B. Dextran sulfate was then admixed to individual wells at a final concentration ranging from 0.01 ug/ml to 50 ug/ml. The first antibody, either a murine monoclonal antibody immunospecific for thyroglobulin or a murine monoclonal antibody immunospecific for CD4 protein was diluted to approximately 4 ug/ml in binding buffer and admixed to each well. The wells were maintained at room temperature for 4 hours in a humidified atmosphere. The wells were then washed 6 times with washing buffer and the excess liquid removed by aspiration. The assay was completed according to Example 1B.

The inhibition of peptide p21-49 binding to immunoglobulin in the presence of various concentrations of dextran sulfate is shown in FIG. 7. Dextran sulfate inhibits the binding of peptide p21-49 to both a monoclonal antibody immunospecific for thyroglobulin (62) and a monoclonal antibody immunospecific for CD4 (OKT4A).

6. Characterization of the CD4-Binding Site on Immunoglobulins.

Figure 8A:
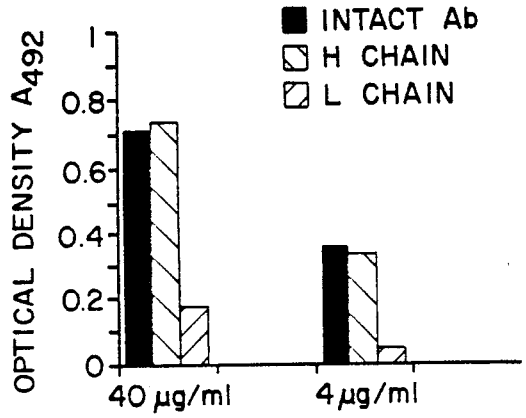
FIG. 8A illustrates the binding of $V_H$-binding peptide p21-49 to intact antibody, isolated Ig heavy chain (H chain) and isolated Ig light chain (L chain).

A series of ELISA assays were performed to localize the peptide p21-49 binding site on immunoglobulin molecules. These assays were similar to the assay described in Example 1B, with the exceptions noted below. Here, the assay described in Example 1B was carried out using isolated immunoglobulin heavy chains instead of the first monoclonal antibody. The isolated immunoglobulin heavy chains were prepared according to the methods described in Zanetti et al, *J. Immunol.*, 135:1245 (1985). The peptide p21-49 bound isolated heavy chain about as well as intact antibody as shown in FIG. 8A.

A similar assay was carried out using isolated immunoglobulin light chain prepared according to the methods described in Zanetti et al., supra, instead of the first monoclonal antibody. The results of this assay, also shown in FIG. 8A, indicate that the light chain did not contribute to immunoglobulin binding by the peptide p21-49.

Figure 8B:
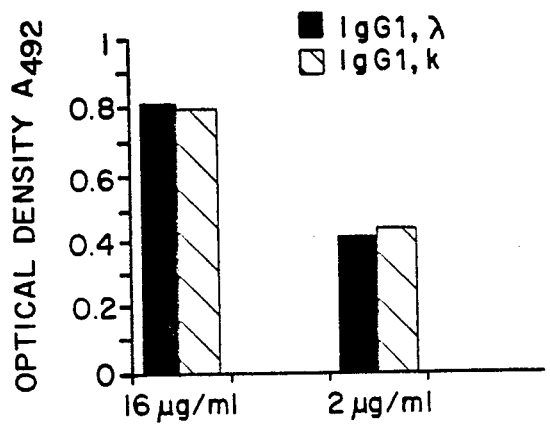
FIG. 8B illustrates the binding of $V_H$-binding peptide p21-49 to chimeric (mouse/human) antibodies of the IgG, (human) isotype with different isotypes of light chain (kappa and lambda).

Further evidence that the binding site for peptide p21-49 was localized to the heavy chain was provided by assays carried out using recombinant chimeric (mouse/human) antibodies of the IgG$_1$(human) isotype with different isotypes of light chain (kappa and lambda). The assay was carried out according to Example 1B except that the first monoclonal antibody was replaced by either recombinant chimeric IgG$_1$-lambda or recombinant chimeric IgG$_1$-kappa antibodies. The assay was completed according to Example 1B and as shown in FIG. 8B, changing the light chain isotype has no effect on the binding of peptide p21-49 to the IgG$_1$ heavy chain. The assays with isolated heavy chain, isolated light chain, and the recombinant chimeric antibodies localize the peptide p21-49 binding to the heavy chain.

Figure 8C:
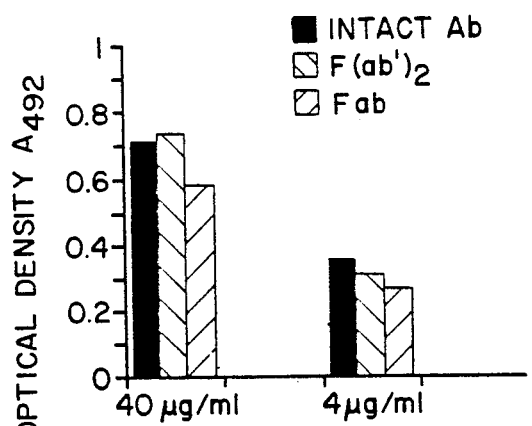
FIG. 8C illustrates the binding of $V_H$-binding peptide p21-49 to intact antibody, F(ab')$_2$ fragments and Fab fragments.

To determine whether peptide p21-49 bound the immunoglobulin heavy chain variable region ($V_H$) or the immunoglobulin heavy chain Fc region, a series of assays utilizing immunoglobulin molecules containing only the variable region [F(ab')$_2$ Fab] were carried out according to Example 1B except that molecules containing only variable regions were used instead of the first monoclonal antibody. Both types of molecules containing only the variable regions [(Fab')$_2$ and Fab] bound peptide p21-49 indicating that the peptide binds somewhere in the variable region of the heavy chain (FIG. 8C).

Figure 8D:
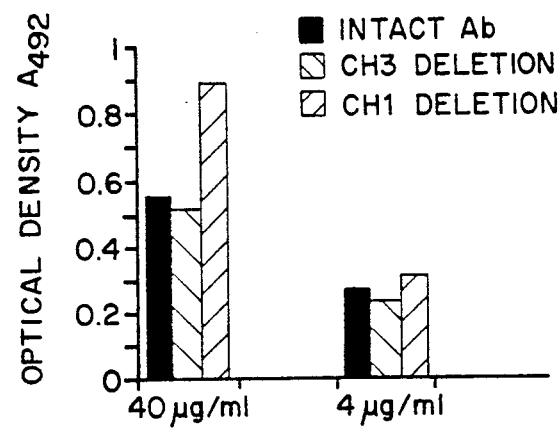
FIG. 8D illustrates the binding of $V_H$-binding peptide p21-49 to mutant antibodies containing deletions in either the CH3 domain or the CH1 domain of the immunoglobulin heavy chain.

Further assays were performed using naturally occurring deletion mutants of MOPC 21, a murine myeloma protein of unknown specificity, that have deleted either the CH$_3$ domain or the CH$_1$ domain of the Ig $V_H$. The assays were carried out according to Example 1B except that the mutant antibodies were used instead of the monoclonal antibody. Neither deletion in the CH$_3$ domain (residues 358–440, *Sequences of Proteins of Immunological Interest*, Kabat et al., U.S. Dept. of Health and Human Services, 4 ed, 1987) nor a deletion in the CH$_1$ domain (residues 121–214, *Sequences of Proteins of Immunological Interest*, Kabat et al., U.S. Dept. of Health and Human Services, 4 ed, 1987) diminished the binding of peptide p21-49 to the immunoglobulin molecules as shown in FIG. 8D. Therefore, peptide p21-49 binds the $V_H$ region of immunoglobulins.

8. Purification of Immunoglobulins Using Peptide P21-49.

The immunoglobulins were purified from an immunoglobulin containing sample using a peptide p21-49 affinity column. The affinity column was prepared by coupling 5 mg of peptide p21-49 to 1 ml of hydrated Sepharose 4B-CNBr activated resin. The peptide was coupled to the Sepharose 4B-CNBr resin according to the manufacturers directions (Pharmacia LKB Biotechnology, Inc., Piscataway, N.J.). Briefly one gram of sepharose 4B-CNBr activated resin was dissolved in 1 mm HCl and maintained for two hours at room temperature. The Sepharose 4B-CNBr was rinsed with the same buffer on a sintered glass filter and then neutralized with 0.1M carbonate buffer at pH 8.3 containing 0.5M NaCl. After the activated Sepharose 4B was neutralized, the resin was collected by centrifugation and peptide p21-49 at a final concentration of 10 mg/ml in 0.1M carbonate buffer at pH 8.3 containing 0.5M NaCl was admixed to the activated resin for 14 hours at 4C. The resin was washed with PBS and the remaining active groups on the Sepharose 4B blocked with glycine by adding glycine to a final concentration of 0.2M at pH 8.0 and maintaining the solution for 2 hours at room temperature. The excess blocking glycine was then washed away with PBS and the coupled resin treated with 0.1M glycine buffer at pH 2.5 followed by treatment with PBS at pH 7.5 containing 0.1% $NaN_3$. The peptide-Sepharose 4B conjugate was stored at 4C until used.

A semi-purified immunoglobulin sample (saturated ammonium sulfate fraction of ascites fluid containing 1 to 2 mg of mouse immunoglobulin) in PBS at PH 7.4 was loaded onto a column containing approximately 1 ml of the packed peptide-Sepharose 4B conjugate resin. The semi-purified sample was allowed to flow slowly through the column allowing the immunoglobulin present in the sample to be bound (segregated into a solid phase) by the immobilized peptide p21-49. After the sample was applied to the column, the column was washed with 2 ml of PBS at pH 7.4 to further segregate the bound immunoglobulins from other non-bound proteins. The bound immunoglobulin was eluted with either 2 ml of 100 mm citric acid at pH 3.0 or a PBS buffer containing dextran sulfate at a final concentration of 50 ug/ml at pH 7.4.

Figure 14:
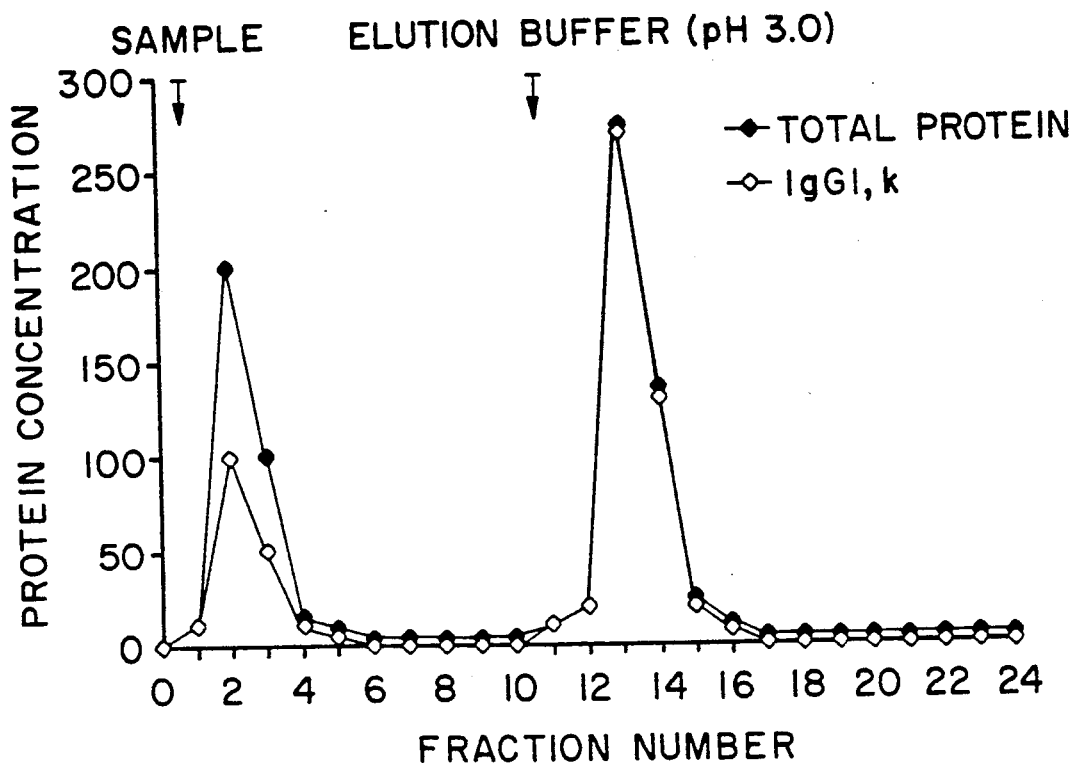
FIG. 14 illustrates the affinity purification of a monoclonal antibody (IgG₁,k) from a complex mixture of proteins (ascites fluid) using a p21-49-Sepharose 4B column. The total protein (solid circles) and IgG₁,k portion of each eluted fraction are shown. The arrows indicate when the sample and elution buffer were applied to the column.

The initial recovery of separated (isolated) immunoglobulin, illustrated in FIG. 14, was about 65% of the applied semi-purified immunoglobulin sample. The isolated immunoglobulin retained all its major biological functions including antigen binding, complement fixation, and its purity was calculated to be greater than 95% pure using sodium dodecyl sulfate-polyacrylamide gel electrophoresis (SDS PAGE).

9. Co-expression of V. Binding Peptide p21-49 with Staphylococcal Protein A $F_c$-Binding Region.

Figure 9:
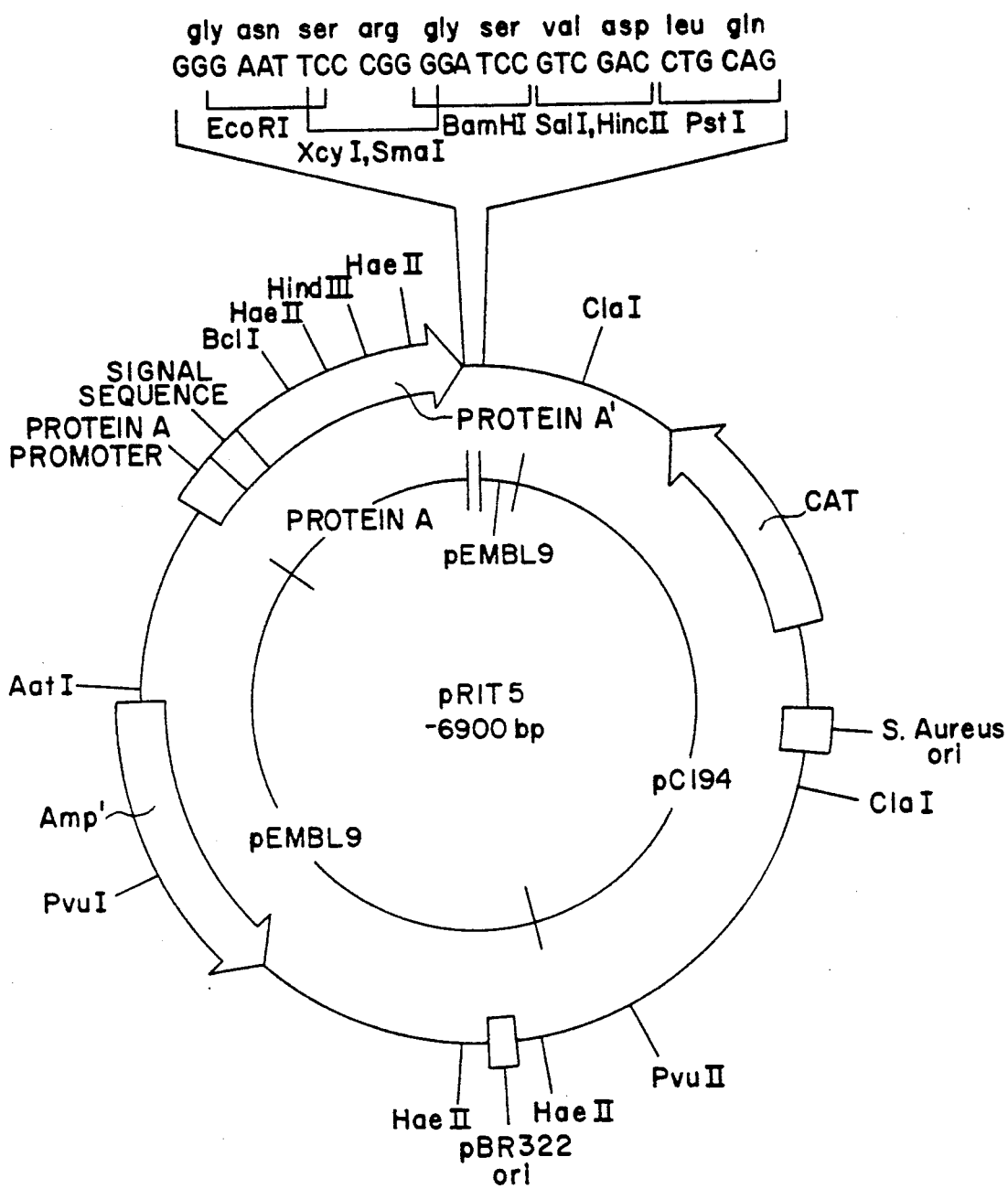
In FIG. 9, the commercially available pRIT5 Protein A gene fusion vector is shown. The plasmid pRIT5 is designed to permit high-level expression of fusion proteins containing the staphylococcal Protein A $F_C$-binding region in both E. coli and S. aureus host cells as described in Nilsson et al., EMBO J., 4:1075 (1985). Genes inserted into the multiple cloning site are expressed from the Protein A promoter and translocated to the periplasmic space in E. coli, or secreted into the growth medium in gram-positive cells. The Protein A promoter and signal sequence are functional in a wide range of bacterial species including both E. coli and S. aureus as described by Uhlen et al., J. Bact., 159:513 (1984). The plasmid also contains the broad-host-range origin of replication and chloramphenicol acetyltransferase gene from pCl94 as described in Horinouchi et al., J. Bact., 150:815 (1982).

A $V_H$-binding protein is expressed with a staphylococcal Protein A $F_C$-binding region by operatively linking a synthetic DNA sequence to a vector designed to express foreign proteins as a fusion protein with the staphylococcal protein A $F_C$-binding region. The pRIT5 protein A gene fusion vector FIG. 9 is commercially available from Pharmacia LKB (Piscataway, N.J.) and is based on the methods and techniques in Nilsson et al., *EMBO J.*, 1075-1080 (1985); and Uhlen et al., *Gene*, 23:369-378 (1983). The pRIT5 protein A gene fusion vector is designed to permit high-level expression of fusion proteins in both *E. coli* and *Staphylococcus aureus* host cells. A gene inserted into the multiple cloning site is expressed from the protein A promoter and translocated to the periplasmic space in *E. coli* or secreted into the growth medium in gram-positive cells such as *Staphylococcus aureus*. The protein A promoter and signal sequence are functional in a wide variety of bacterial species including *S. aureus* strain SA113 described in Uhlen et al., *J. Bact.*, 159:713 (1984). The pRIT5 vector contains the broad-host-range origin of replication and the chloramphenicol acetyl transferase gene from PC194 described in Horincuehi et al., *J. Bact.*, 150:815 (1982).

A synthetic DNA sequence coding for the $V_H$-binding peptide p21-49 with Bam HI restriction endonuclease (restriction enzyme) sites attached to the ends is constructed by synthesizing the following polynucleotides using an Applied Biosystem DNA Synthesizer and following the manufactures instructions (Applied Biosystems, Foster City, Calif.).

01—GATCCCAAAAAAAAAGTATCCAATT-CCATTGGAAAAACAGTAACAGTAAC-CAAAT
02—CAAAATCTTAGGTAACCAAGG-TAGTTTCTTAACTAAAGGTCCTAGTG
03—AATGGAATTGGATACTTTTTTTTTG
04—TAAGATTTTGATTTGGT-TACTGTTTTTCC
05—TGCAGACTAGGACCTTTCGT-TAAGAAACTACCTTGGTTACC

These polynucleotides are designed to hybridize to each other and form the double stranded sequence shown in FIG. 10.

Polynucleotides 02, 03, 03 and 04 are kinased by adding 1 ul of 100 ug/ml solution of each of the polynucleotides, 20 units of T4 polynucleotide kinase to a solution containing 70 mm tris(Hydroxymethyl]aminomethane (Tris-HCl) at pH 7.6, 10 mM $MgCl_2$ 5 mM dithiothreitol (DTT), 10 MM 2-mercaptoethanol (2 ME), 500 mg/ml of bovine serum albumin (BSA). The solution is maintained at 37° C. for about 30 minutes and the reaction stopped by maintaining the solution at 65C for 10 minutes. The two end polynucleotides, 20 ng of polynucleotide 01 and 20 ug polynucleotide 05, are added to the above kinasing reaction solution together with 1/10 volume of a solution containing 20.0 mM Tris-HCl at pH 7.4, 2.0 MM $MgCl_2$ and 15.0 MM NaCl. This solution is heated to 70° C. for 5 minutes and allowed to cool to room temperature, approximately 25° C., over 1.5 hours in a 500 ml beaker of water. During this time period all the polynucleotides anneal to form the double stranded synthetic DNA insert. The individual polynucleotides are covalently linked to each other to stabilize the synthetic DNA insert by adding 40 ul of the above reaction to a solution containing 50 mM Tris-HCl at pH 7.5, 7 MM $MgCl_2$, 1 MM DTT, 1 MM ATP and 10 units of T4 DNA ligase. This solution is maintained at 37° C. for 30 minutes and then the T4 DNA ligase is inactivated by maintaining the solution at 65° C. for 10 minutes. The end polynucleotides are kinased by mixing 52 ul of the above reaction, 4 ul of a solution containing 10 MM ATP and 5 units of T4 polynucleotide kinase. The solution is maintained at 37° C. for 30 minutes and then the T4 polynucleotide kinase is inactivated by maintaining the solution at 65° C. for 10 minutes.

The completed synthetic DNA insert shown in FIG. 10, is ligated directly into the pRIT5 protein A gene fusion vector that has been previously digested with the restriction endonuclease Bam HI followed by alkaline phosphatase treatment to remove 5'-terminal phosphates. The ligation mixture is then transformed into suitable host cells and plated out to produce single colony transformants. DNA is prepared from several of the resulting single colony transformants and the DNA sequence of the synthetic DNA insert coding for the $V_H$-binding peptide determined using methods similar to or dependent on the chain termination DNA sequencing methodology described by Sanger et al., *Proc. Natl. Acad. Sci., USA*, 74:5463-5467 (1973). This DNA sequencing confirms the accuracy of the above construction steps.

The protein A F$_C$-binding:V$_H$-binding peptide p21-49 fusion protein is expressed in *E. Coli* and *S. aureus* using methods similar to the methods described in Nilsson et al., *EMBO J.*, 4:1075-1080 (1985); and Uhlen et al., *Gene*, 23:369-378 (1983).

The level of expression of the protein A F$_C$-binding:V$_H$-binding peptide p21-49 is determined using an ELISA assay capable of detecting the immunoglobulin binding peptide p21-49 in host cell extracts and on host cell membranes.

10. Co-expression of V.-binding Peptide P21-49 With Streptococcal Protein G F$_C$-binding Region.

Figure 11:
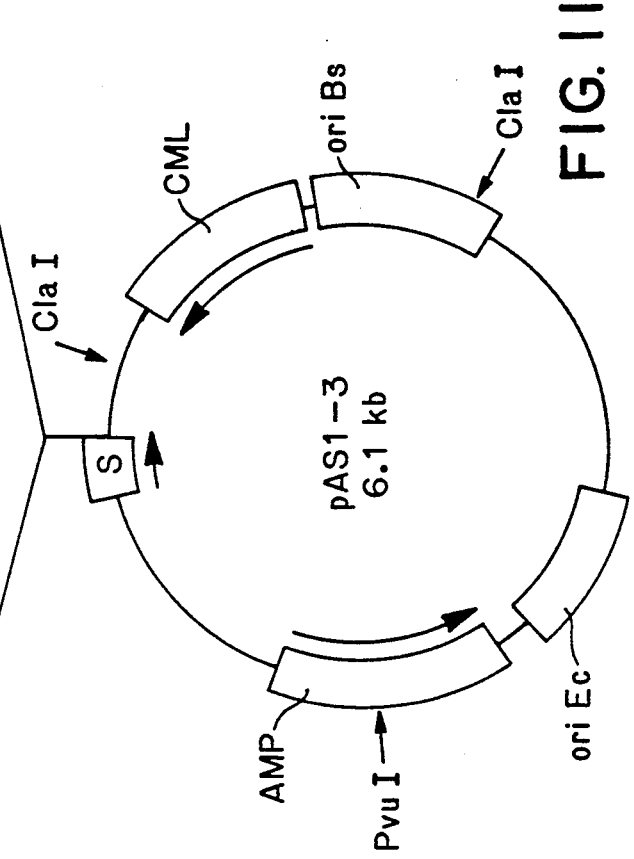
In FIG. 11, the pASI-3 expression vectors containing the staphylococcal Protein A promoter and signal sequence described in Abrahmsen et al., EMBO J., 4:3901-3906 (1985) is shown. The pASI-3 vector series is designated to permit high level expression of a gene inserted into the multiple cloning site in both E. coli and S. aureus host cells. Boxes represent the position of the genes coding for the staphylococcal Protein A signal sequence (s), the B-bactamase (Amp) and chloramphenicol acetyl transferase (cml). The origins of replication in E. coli (oriEC) and in staphylococci/bacilli (oriBS) are also shown.

The V$_H$-binding peptide p21-49 is expressed with streptococcal protein G F$_C$-binding region by operatively linking a synthetic DNA sequence coding for the F$_C$-binding region of streptococcal G to one of the vectors, shown in FIG. 11, containing the staphylococcal Protein A promoter and signal sequence described in Abrahmsen et al., *EMBO J.*, 4:3901-3906 (1985). The vector series, pAS1-3 is designed so that a foreign gene can be inserted directly following the staphylococcal protein A signal sequence and thus the gene will be expressed as a fusion protein with the staphylococcal protein A signal sequence at its N-terminus. The pAS1-3 vector series is designed to permit high level expression of such fusion proteins in both *E. coli* and *Staphylococcus Aureus* host cells. A gene inserted into the multiple cloning site is expressed from the Protein A promoter and translated to the periplasmic in *E. coli* or secreted into the growth medium in gram-positive cells such as *Staphylococcus aureus*. The Protein A promoter and signal sequence are functional in a wide variety of bacterial species including *S. aureus* strain SA113 described in Uhlen et al., *J. Bact.*, 159:713 (1984). The pAS 1-3 series of vectors contain both the origin of replication from *E. coli* and the origin of replication from *Staphylococci/Bacilli* thus allowing the vectors to be grown in a wide range of host cells. The pAS 1-3 series of vectors also contain the chloramphenicol acetyl transferase gene from PC194 described in Horincuehi et al., *J. Bact.*, 150:815 (1982).

A synthetic DNA sequence coding for the binding portion of streptococcal protein G with a Eco RI restriction enzyme site on the ends is constructed by synthesizing the following polynucleotides using an Applied Biosystems DNA Synthesizer and following the manufacturers instructions (Applied Biosystems, Foster City, Calif.).

G1—AATTCATCGATGCGTCTGAATTAACACCAGCCGTGACAACT
G2—ACAAACTTGTTATTAATGGTAAAACATTGAAAGGCGAAACA
G3—CTACTGAAGCTGTTGATGCTGCTACTGCAGAAAAGTCTT
G4—CAAACAATACGCTAACGACAACGGTGTTGACGGTGAATGG
G5—ACTTACGACGATGCGACTAAGACCTTTACAGTTACTGAAA
G6—AACCAGAAGTGATCGATGGATCCG
G7—TTAATTCAGACGCATCGATG
G8—TTACCATTAATAACAAGTTTGTAAGTTGTCACGGCTGGTG
G9—AGCATCAACAGCTTCAGTAGTTGTTTCGCCTTTCAATGTT
G10—TGTCGTTAGCGTATTGTTTGAAGACTTTTTCTGCAGTAGC
G11—TAGTCGCATCGTCGTAAGTCCATTCACCGTCAACACCAT
G12—AATTCGGATCCATCGATCACTTCTGGTTTTTCAGTAACTGTAAAGGTCT

These polynucleotides are designed to hybridize to each other and form the double stranded DNA sequence shown in FIG. 12.

Polynucleotides G2 through G11 are kinased by adding one ul of a 100 ug/ml solution of each of the nucleotides, 20 units of T4 polynucleotide kinase to a solution containing 70 MM Tris-HCl at pH 7.6, 10 MM MgCl$_2$, 5 mm DDT, 10 mm 2ME, 500 ug/ml of BSA. The solution is maintained at 37° C. for about 30 min and the reaction stopped by maintaining the solution at 65° C. for 10 minutes. The two end polynucleotides 20 ng of polynucleotide G1 and polynucleotide G12 are added to the above kinasing reaction solution together with 1/10 volume of a solution containing 20 MM Tris-HCl at pH 7.4, 2 MM MgCl$_2$ and 15 MM NaCl. This solution is heated to 70° C. for five minutes and allowed to cool to room temperature, approximately 25° C., over 1.5 hours in a 500 ml beaker of water. During this time all the polynucleotides anneal to form the double stranded synthetic DNA insert. The individual polynucleotides are covalently linked to each other to stabilize the synthetic insert by adding 40 ul of the above reaction mixture to a solution containing 50 MM Tris-HCl at pH 7.5, 7 MM MgCl$_2$, 1 mM DTT, 1 mm ATP and 10 units of T4 DNA ligase. This solution is maintained at 37° C. for 30 minutes and then the T4 DNA ligase is inactivated by maintaining the solution at 65° C. for 10 minutes. The end polynucleotides are kinased by mixing 52 ul of the above reaction, 4 ul of a solution containing 10 mm ATP and 5 units of T4 polynucleotide kinase. The solution is maintained at 37° C. for thirty minutes and then the T4 polynucleotide kinase is inactivated by maintaining the solution at 65° C. for 10 minutes.

The completed DNA insert is ligated directly into the pAS1 vector that has been previously digested with the restriction enzyme Eco RI followed by treatment with alkaline phosphatase to remove 5'-terminal phosphate groups. The ligation mixture is then transformed into suitable host cells and plated out to produce single colony transformants. DNA is prepared from several of the resulting single colony transformants and the DNA sequence of the synthetic DNA insert coding for the Protein G F$_C$-binding region is determined using methods similar to, or dependent on the chain termination DNA sequencing methodology described by Sanger et al., *Proc. Natl. Acad. Sci., USA*, 74:5463-5467 (1973). This DNA sequencing confirms the accuracy of the above construction steps.

The synthetic DNA insert constructed above and shown in FIG. 12 contains a unique Bam HI restriction enzyme site. The new vector resulting from the above construction steps is linearized at this unique Bam HI site and the synthetic DNA sequence coding for the V$_H$-binding peptide p21-49 constructed in Example 9 (FIG. 10) is ligated into this site. This ligation mixture is then transformed into suitable host cells and DNA is prepared from several of the resulting single colony transformants. The DNA sequence of the two synthetic DNA inserts and the regions surrounding them are determined using the chain termination DNA sequencing methodology. The resulting vector is able to co-express Protein G F$_C$-binding region and V$_H$-binding peptide p21-49 as a fusion protein with the signal sequence from staphlacoccal Protein A.

The protein G $F_C$-binding region:$V_H$-binding peptide fusion protein is expressed in *E. coli* and *S. aureus* using methods similar to the methods described in Nilsson et al., *EMBO J.*, 4:1075–1080 (1985); and Uhlen et al., *Gene*, 23:369–378 (1983).

The level of expression of the protein G $F_C$-binding:$V_H$-binding peptide is determined using an ELISA assay capable of detecting the immunoglobulin binding peptide p21-49 in host cells extracts and on host cell membranes.

11. Co-expression of $V_H$-binding peptide P21-49 With Staphylococcal Protein A and Streptococcal Protein G-$F_C$-binding Regions.

$V_H$-binding protein 21-49 is expressed with $F_C$-binding regions derived from both Staphylococcal protein A and Streptococcal protein G by operatively linking a synthetic DNA sequence containing the $F_C$-binding region of Streptococcal protein G to a vector designed to express foreign proteins as a fusion protein with the Staphylococcal protein A $F_C$-binding region. The pRIT5 protein A gene fusion vector (FIG. 9) is commercially available from Pharmacia LKB (Piscataway, N.J.) and is based on the methods and techniques described in Nilsson et al., *EMBO J.*, 1075–1080 (1985); and Uhlen et al., Gene, 23:369–378 (1983). A synthetic DNA sequence coding for the $F_C$-binding portion of protein G with 5′ overhanging ends compatible with a Bam HI restriction site was constructed by synthesizing the following polynucleotides using an Applied Biosystems DNA Synthesizer and following the manufacturers instructions (Applied Biosystems, Foster City, Calif.).

GA1—GATCCATCGATGCGTCTGAAT-TAACACCAGCCGTGACAACTTACAAA
GA2—CTTGTTATTAATGGTAAAACATT-GAAAGGCGAAACAACTACT
GA3—GAAGCTGTTGATGCTGCTACT-GCAGAAAAAGTCTTCAAACAA
GA4—TACGCTAACGACAACGGTGTT-GACGGTGAATGGACTTACGACGAT
GA5—GCGACTAAGACCTTTACAGTTACT-GAAAAACCAGAAGTGATCGATGGATCC
GA6—TGTTAATTCAGACGCATCGAT
GA7—TGTTTTACCATTAATAACAAGTTT-GTAAGTTGTCACGGCTGG
GA8—AGTAGCAGCATCAACAGCTTCAG-TAGTTGTTTCGCCTTTCAA
GA9—GTCAACACCGTTGTCGTTAGC-GTATTGTTTGAAGACTTTTTCTGC
GA10—AACTGTAAAGGTCTTAGTC-GCATCGTCGTAAGTCCATTCACC
GA11—GGATCGGGATCCATCGAT-CACTTCTGGTTTTTCAGT

These polynucleotides are designed to hybridize to each other to form the double stranded DNA sequence shown in FIG. 13.

Polynucleotides GA2 through GA10 are kinased by adding 1 ul of a 100 ug/ml solution of each of the polynucleotides, 20 units of T4 polynucleotide kinase to a solution containing 70 MM Tris-HCl at pH 7.6, 10 mm MgCl$_2$, 5 mM DTT, 10 mM 2ME, and 500 ug/ml of BSA. The solution is maintained at 37° C. for 30 minutes and the reaction stopped by maintaining the solution at 65° C. for 10 minutes. The 2 end polynucleotides, 20 ng of polynucleotide GA1 and 20 ng of polypeptide GA11 are added to the above kinasing reaction solution together with 1/10 volume of a solution containing 20 MM Tris-HCl at pH 7.4, 2 MM MgCl$_2$ and 15 mM NaCl. This solution is heated to 70° C. for 5 minutes and allowed to cool to room temperature, approximately 25° C., over 1.5 hours in a 500 ml beaker of water. During this time all the polynucleotides anneal to form the double stranded synthetic DNA insert shown in FIG. 10. The individual polynucleotides are covalently linked to each other to stabilize the synthetic DNA insert by adding 40 ul of the above reaction to a solution containing 50 MM Tris-HCl at pH 7.5, 7 MM MgCl$_2$, 1 mM DTT, 1 mm ATP and 10 units of T4 DNA ligase. This solution is maintained at 37° C. for 30 minutes and then the T4 DNA ligase inactivated by maintaining the solution at 65° C. for 10 minutes. The end polynucleotides are kinased by mixing 52 ul of the above reaction, 4 ul of a solution containing 10 MM ATP and 5 units of T4 polynucleotide kinase. The solution is maintained at 37° C. for 30 minutes and then the T4 polynucleotide kinase inactivated by maintaining the solution at 65° C. for 10 minutes.

The completed DNA insert is ligated directly into the pRIT5 protein A gene fusion vector shown in FIG. 11 that has been previously digested with the restriction endonuclease Bam HI. The ligation mixture is then transformed into suitable host cells and DNA is prepared from the resulting single colony transformants. The sequence of the synthetic DNA insert coding for the Protein G $F_C$-binding portion is determined using methods similar to or dependent on the chain termination sequencing methodology described by Sanger et al., *Proc. Natl. Acad. Sci.*, USA, 74:5463–5467 (1973). This DNA sequencing confirms the accuracy of the above construction steps.

The synthetic DNA insert constructed above (FIG. 13), when inserted into the Bam HI site of pRIT5 vector renders this Bam HI site uncuttable with Bam HI. The synthetic DNA insert however contains a new Bam HI site. The synthetic DNA insert prepared in Example 9 containing the $V_H$-binding peptide p21-49 is inserted into this new Bam HI site. This is done by digesting the vector constructed above with the restriction endonuclease Bam HI and ligating the synthetic DNA insert constructed in Example 9 into this vector. The ligation mixture is then transformed into suitable host cells and DNA prepared from the resulting single colony transformants. The DNA sequence of the entire synthetic DNA insert coding for both the Protein G $F_C$-binding portion and the $V_H$-binding peptide p21-49 is determined using the chain termination DNA sequencing methodology. This second round of DNA sequencing confirms the overall accuracy of the series of construction steps performed to generate a vector capable of expressing the Protein G $F_C$-binding portion together with both the Protein A $F_C$-binding portion and the $V_H$-binding peptide p21-49. The Protein A $F_C$-binding region:Protein G $F_C$-binding region:$V_H$-binding peptide p21-49 fusion protein is expressed in either *E. coli* or *S. aureus* using methods similar to the methods described in Nilsson et al., *EMBO J.*, 4:1075–1080 (1985); and Uhlen et al., *Gene*, 23:369–378 (1983).

The level of expression of the Protein A $F_C$-binding region:Protein G $F_C$-binding region:$V_H$-binding peptide p21-49 fusion protein is determined using an ELISA assay capable of detecting the $V_H$-binding peptide p21-49 in host cell extracts and on host cell membranes.

The foregoing specification, including the specific embodiments and examples, is intended to be illustrative

What is claimed is:

1. A method of separating immunoglobulin molecules from an aqueous sample, which method comprises the steps of:
   (a) admixing said aqueous sample with a polypeptide comprising a single polypeptide chain having a $V_H$-binding segment, selected from the group consisting of:
   (A) NH$_2$-Lys-Lys-Ser-Ile-Gln-Phe-His-Trp-Lys-Asn-Ser-Asn-Gln-Ile-Lys-Ile-Leu-Gly-COOH,
   (B) NH$_2$-Lys-Lys-Ser-Ile-Gln-Phe-His-Trp-Lys-Asn-Ser-Asn-Gln-Ile-Lye-Ile-Leu-Gly-Asn-Gln-Gly-Ser-Phe-Leu-Thr-Lys-Gly-Pro-Ser-COOH,
   (C) NH$_2$-Lys-Ser-Ile-Gln-Phe-His-Trp-Lys-Asn-Ser-Asn-Gln-Ile-Lys-Ile-Leu-Gly-COOH,
   (D) NH$_2$-Ser-Ile-Gln-Phe-His-Trp-Lys-Asn-Ser-Asn-Gln-Ile-Lye-Ile-Leu-Gly-COOH,
   (E) NH$_2$-Ile-Gln-Phe-His-Trp-Lys-Asn-Ser-Asn-Gln-Ile-Lys-Ile-Leu-Gly-COOH, and
   (F) NH$_2$-Lys-Lys-Ser-Ile-Gln-Phe-His-Trp-Lys-Asn-Ser-Asn-Gln-Ile-Lys-Ile-Leu-COOH,
   (b) maintaining said admixture under Ig-binding conditions to form a binding reaction admixture including a temperature of about 4° C. to about 45° C., a pH value of about 5 to about 9 and an ionic strength of no more than that equivalent to about one molar of sodium chloride for a time period sufficient for a portion of said immunoglobulin molecules present to bind said polypeptide to form a complex and a non-bound sample portion; and
   (c) segregating said complex from said non-bound sample portion, thereby separating said immunoglobulin molecules from said aqueous sample.

2. The method of claim 1 wherein said non-bound sample portion is recovered.

3. A method of separating immunoglobulin molecules from an aqueous sample, which method comprises the steps of:
   (a) admixing said aqueous sample with a polypeptide that exhibits antigen-independent affinity for a $V_H$ region of antibody molecule, said polypeptide being free from a binding site for a human immunodeficiency virus, said polypeptide having an amino acid sequence represented by at least one of the formulae selected from the group consisting of:
   (A) NH$_2$-Lys-Lys-Ser-Ill-Gln-Phe-His-Trp-Lys-Asn-Ser-Asn-Gln-Ile-Lys-Ile-Leu-Gly-COOH,
   (B) NH$_2$-Lys-Lys-Ser-Ile-Gln-Phe-His-Trp-Lys-Asn-Ser-Asn-Gln-Ile-Lye-Ile-Leu-Gly-Asn-Gln-Gly-Ser-Phe-Leu-Thr-Lys-Gly-Pro-Ser-COOH,
   (C) NH$_2$-Lys-Ser-Ile-Gln-Phe-His-Trp-Lys-Asn-Ser-Asn-Gln-Ile-Lys-Ile-Leu-Gly-COOH,
   (D) NH$_2$-Ser-Ile-Gln-Phe-His-Trp-Lys-Asn-Ser-Asn-Gln-Ile-Lye-Ile-Leu-Gly-COOH,
   (E) NH$_2$-Ile-Gln-Phe-His-Trp-Lys-Asn-Ser-Asn-Gln-Ile-Lys-Ile-Leu-Gly-COOH, and
   (F) NH$_2$-Lys-Lys-Ser-Ile-Gln-Phe-His-Trp-Lys-Asn-Ser-Asn-Gln-Ile-Lys-Ile-Leu-COOH,
   to form a binding reaction mixture;
   (b) maintaining said admixture under Ig-binding conditions that maintain the biological activity of the polypeptide and the antibodies sought to be bound including a temperature of about 4° C. to about 45° C., a pH value of about 5 to about 9 and an ionic strength of no more than that equivalent to about one molar of sodium chloride for a time period sufficient for a portion of said immunoglobulin molecules present to bind said polypeptide to form a complex and a non-bound sample portion; and
   (c) segregating said complex from said non-bound sample portion, thereby separating said immunoglobulin molecules from said aqueous sample.

4. The method of claim 3 wherein said non-bound sample portion is recovered.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 3, line 36, after "binding to", change "Fc" to --$F_c$--.

In Col. 5, line 66, after "series of", change "not" to --no--.

In Col. 6, Table 1, line 58, after "p24-", change "NH" to --$NH_2$--.

In Col. 7, line 5, after "herein", insert the following --in which one or more residues have been--.

In Col. 7, line 65, after "Groups in", change "organic chemistry" to --Organic Chemistry--.

In Col. 10, line 3, after "binding the", change "F," to --$F_c$--.

In Col. 10, Table 2, after the third line sequence in "Peptide (F)$^3$", add the following fourth line sequence:

--Asn-Asp-Asn-Gly-Val-Asp-Gly-Val-Trp-Thr-Tyr--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 11, Table 2-continued, after the third line sequence in "Peptide $(L)^8$", delete the next three lines of sequences beginning with "-Ala-Asp..." and ending with "-Gln-Ser", as they are a repeat of the first three lines of sequences.

In Col. 14, line 25, after "DNA molecule", change "(RDNA)" to --(rDNA)--.

In Col. 14, line 62, after "plasmids are", change "pUCs, pUCs," to --pUC8, pUC9--.

In Col. 15, line 6, after "vectors are" change "PSVL" to --pSVL--.

In Col. 16, line 6, after "preferably an", change "RDNA" to --rDNA--.

In Col. 16, line 26, after "Maniatis et al.,", change *Molecular Clonin* to --*Molecular Cloning*,--.

In Col. 16, line 38, after "introduction of an", change "RDNA" to --rDNA--.

UNITED STATES PATENT AND TRADEMARK OFFICE
CERTIFICATE OF CORRECTION

PATENT NO. : 5,306,812  Page 3 of 8
DATED : April 26, 1994
INVENTOR(S) : ZANETTI, M., et al.

It is certified that error appears in the above-indentified patent and that said Letters Patent is hereby corrected as shown below:

In Col. 16, line 42, after "presence of the", change "RDNA" to --rDNA--.

In Col. 16, line 46, change "RDNA" to --rDNA--.

In Col. 16, line 47, after "when the", change "RDNA" to --rDNA--.

In Col. 18, line 15, after "Table 4.", change "one" to --One--.

In Col. 19, line 3, after "dissociation of the", delete "complex, of course," and insert --complex. Of course,--.

In Col. 19, line 23, after "and any", change "V," to --$V_H$--.

In Col. 19, line 43, after "but the", change "Method" to --method--.

In Col. 19, line 50, after "Peptide", change "D16-49" to --p16-49--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 19, line 63, after "Peptide", change P21-49" to --p21-49--.

In Col. 20, line 11, after "containing", delete "TWEEN" and insert the following --0.5% polyoxyethylensorbitan monolaurate (TWEEN-20)--.

In Col. 21, line 16, after "Peptide", change "P21-49" to --p21-49--.

In Col. 21, line 48, after "peptide", change "P21-49" to --p21-49--.

In Col. 21, line 53, after "peptide", change "P21-49" to --p21-49--.

In Col. 22, Table 4, in Designation p 66-90, delete the last group of sequences "YEDQK" and insert therefore --Y--.

In Col. 22, line 52, after "Peptide", change "P21-49" to --p21-49--.

In Col. 23, line 34, after "Peptide", change "v21-49" to --p21-49--.

In Col. 24, line 31, after "[F(ab')$_2$" insert --and--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 24, lines 55 and 56, after "Peptide", change "P21-49" to --p21-49--.

In Col. 24, line 66, change "mm" to --mM--.

In Col. 25, line 30, after "100", change "mm" to --mM--.

In Col. 25, line 41, after "Co-expression of", change "V." to --$V_H$.--.

In Col. 26, line 24, after "70", change "mm" to --mM--.

In Col. 26, line 26, after "10", change "MM" to --mM--.

In Col. 26, line 34, change "MM", both occurrences, to --mM--.

In Col. 26, line 43, change "MM", all occurrences, to --mM--.

In Col. 26, line 49, change "MM" to --mM--.

In Col. 27, line 11, after "Co-expression of", change "V.-binding" to --$V_H$-binding--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 27, line 11, after "Peptide", change "P21-49" to --p21-49--.

In Col. 28, line 11, change "MM", both occurrences, to --mM--.

In Col. 28, line 18, after "20", change "MM" to --mM--.

In Col. 28, line 19, change "MM", both occurrences, to --mM--.

In Col. 28, line 27, after "50", change "MM" to --mM--.

In Col. 28, line 28, after "7", change "MM" to --mM--.

In Col. 28, line 28, after "1", change "mm" to --mM--.

In Col. 28, line 33, after "10", change "mm" to --mM--.

In Col. 29, line 11, after "peptide", change "P21-49" to --p21-49--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 29, line 61, after "70", change "MM" to --mM--.

In Col. 29, line 61, after "10", change "mm" to --mM--.

In Col. 30, line 1, change "MM", both occurrences, to --mM--.

In Col. 30, line 10, change "MM", both occurrences", to --mM--.

In Col. 30, line 11, after "1", change "mm" to --mM--.

In Col. 30, line 16, after "10", change "MM" to --mM--.

UNITED STATES PATENT AND TRADEMARK OFFICE
CERTIFICATE OF CORRECTION

PATENT NO. : 5,306,812
DATED : April 26, 1994
INVENTOR(S) : ZANETTI, M., et al.

It is certified that error appears in the above-indentified patent and that said Letters Patent is hereby corrected as shown below:

In Col. 32, Claim 3, line 11, after "-Ser-", change "Ill" to --Ile--.

Signed and Sealed this

Twenty-fifth Day of October, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. :  5,306,812
DATED      :  April 26, 1994
INVENTOR(S):  ZANETTI, M., et al.

It is certified that error appears in the above-indentified patent and that said Letters Patent is hereby corrected as shown below:

In Col. 3, line 68, after "with", change "in" to --an--.

In Col. 9, line 33, after "-Lys-", change "Ileu-" to --Ile--.

In Col. 13, line 6, after "about 5", change "orout" to --about--.

In Col. 18, line 9, after "contemplated is a", change "$_vH$-binding" to --$V_H$-binding--.

Signed and Sealed this

Twenty-second Day of November, 1994

Attest:

BRUCE LEHMAN

Attesting Officer

Commissioner of Patents and Trademarks